(12) United States Patent
Chiou et al.

(10) Patent No.: US 9,364,831 B2
(45) Date of Patent: Jun. 14, 2016

(54) PULSED LASER TRIGGERED HIGH SPEED MICROFLUIDIC SWITCH AND APPLICATIONS IN FLUORESCENT ACTIVATED CELL SORTING

(75) Inventors: Pei-Yu Chiou, Los Angeles, CA (US); Ting-Hsiang Wu, Los Angeles, CA (US); Michael A. Teitell, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 206 days.

(21) Appl. No.: 12/852,320

(22) Filed: Aug. 6, 2010

(65) Prior Publication Data

US 2011/0030808 A1 Feb. 10, 2011

Related U.S. Application Data

(60) Provisional application No. 61/232,416, filed on Aug. 8, 2009.

(51) Int. Cl.
| | |
|---|---|
| *G01N 15/10* | (2006.01) |
| *B01L 3/00* | (2006.01) |
| *F16K 99/00* | (2006.01) |
| *G01N 15/14* | (2006.01) |

(52) U.S. Cl.
CPC ..... *B01L 3/502738* (2013.01); *B01L 3/502761* (2013.01); *F16K 99/0001* (2013.01); *F16K 99/004* (2013.01); *F16K 99/0026* (2013.01); *F16K 99/0028* (2013.01); *F16K 99/0061* (2013.01); *B01L 2200/0636* (2013.01); *B01L 2200/0652* (2013.01); *B01L 2300/0816* (2013.01); *B01L 2300/0864* (2013.01); *B01L 2300/123* (2013.01); *B01L 2400/0442* (2013.01); *B01L 2400/0454* (2013.01); *B01L 2400/0622* (2013.01); *B01L 2400/0655* (2013.01); *F16K 2099/0084* (2013.01); *G01N 15/1459* (2013.01); *G01N 2015/149* (2013.01); *Y10T 137/0391* (2015.04); *Y10T 137/2224* (2015.04)

(58) Field of Classification Search
USPC .......... 209/631, 155; 422/502–504, 507, 509; 137/13, 833
See application file for complete search history.

(56) References Cited

U.S. PATENT DOCUMENTS

| | | | |
|---|---|---|---|
| 6,143,496 | A | 11/2000 | Brown et al. |
| 7,582,482 | B2 | 9/2009 | Dasgupta et al. |
| 8,062,903 | B2 | 11/2011 | Chiu et al. |
| 8,127,624 | B2 | 3/2012 | Hashimoto et al. |

(Continued)

FOREIGN PATENT DOCUMENTS

| | | |
|---|---|---|
| WO | WO 2012/009320 A2 | 1/2012 |
| WO | WO 2013/120016 A2 | 8/2013 |

OTHER PUBLICATIONS

U.S. Office Action dated Jan. 2, 2014 issued in U.S. Appl. No. 13/370,196.

(Continued)

*Primary Examiner* — Paul Hyun
(74) *Attorney, Agent, or Firm* — Tomm Hunter; Weaver Austin Villeneuve & Sampson LLP

(57) ABSTRACT

In certain embodiments this invention provides a pulsed-laser triggered microfluidic switching mechanism that can achieve a switching time of 70 μs. This switching speed is two orders of magnitude shorter than that of the fastest switching mechanism utilized in previous μFACS.

17 Claims, 18 Drawing Sheets

(56) References Cited

U.S. PATENT DOCUMENTS

| | | | |
|---|---|---|---|
| 8,136,553 | B2 | 3/2012 | Baroud et al. |
| 8,206,994 | B2 | 6/2012 | Baroud |
| 8,268,633 | B2 | 9/2012 | Ramsey et al. |
| 8,383,061 | B2 | 2/2013 | Prakash et al. |
| 8,506,905 | B2 | 8/2013 | Takeuchi et al. |
| 8,506,907 | B2 | 8/2013 | Angelescu |
| 8,563,325 | B1 | 10/2013 | Bartsch et al. |
| 8,592,215 | B2 | 11/2013 | Quake et al. |
| 9,176,504 | B2 | 11/2015 | Chiou et al. |
| 2002/0005354 | A1* | 1/2002 | Spence et al. ............ 204/450 |
| 2002/0029814 | A1* | 3/2002 | Unger et al. ............ 137/824 |
| 2002/0037499 | A1* | 3/2002 | Quake et al. ............ 435/5 |
| 2003/0198523 | A1* | 10/2003 | Bohm et al. ............ 406/198 |
| 2006/0177348 | A1* | 8/2006 | Yasuda et al. ............ 422/73 |
| 2008/0032295 | A1* | 2/2008 | Toumazou et al. ............ 435/6 |
| 2008/0196778 | A1 | 8/2008 | Baroud et al. |
| 2009/0090422 | A1 | 4/2009 | Baroud et al. |
| 2011/0059556 | A1 | 3/2011 | Strey et al. |
| 2011/0114190 | A1 | 5/2011 | Wen et al. |
| 2011/0177586 | A1 | 7/2011 | Ismagilov et al. |
| 2012/0236299 | A1 | 9/2012 | Chiou et al. |
| 2013/0183210 | A1 | 7/2013 | Wiyatno et al. |
| 2014/0212986 | A1 | 7/2014 | Angelescu et al. |

OTHER PUBLICATIONS

PCT International Search Report and Written Opinion dated Dec. 20, 2013 issued in PCT/US2013/025434.

Applegate, Jr. et al., (2006) "Microfluidic sorting system based on optical waveguide integration and diode laser bar trapping," *Lab on a Chip*, 6:422-426 [Downloaded by University of California—Los Angeles on Apr. 18, 2013 19:29:53. Published on Jan. 20, 2006 on http://pubs.rsc.org | doi:10.1039/B512576F].

Baret et al., (2009) "Fluorescence-activated droplet sorting (FADS): efficient microfluidic cell sorting based on enzymatic activity," *Lab on a Chip*, 9:1850-1858. [Downloaded by University of California—Los Angeles on Apr. 18, 2013 19:18:09. Published on Apr. 23, 2009 on http://pubs.rsc.org | doi:10.1039/B902504A].

Chiou et al., (Jul. 21, 2005) "Massively parallel manipulation of single cells and microparticles using optical images," *Nature*, 436:370-372. [doi:10.1038/nature03831].

Cho et al., (2010) "Human mammalian cell sorting using a highly integrated micro-fabricated fluorescence-activated cell sorter (µFACS)," *Lab on a Chip*, 10:1567-1573. [Downloaded by University of California—Los Angeles on Apr. 18, 2013 19:31:47. Published on Apr. 9, 2010 on http://pubs.rsc.org | doi:10.1039/C000136H].

Di Carlo et al., (Nov. 27, 2007) "Continuous inertial focusing, ordering, and separation of particles in microchannels," *PNAS of the United States of America*, 104(48):18892-18897.

El-Sayed et al., (2006) "Selective laser photo-thermal therapy of epithelial carcinoma using anti-EGFR antibody conjugated gold nanoparticles," *Cancer Letters*, 239:129-135.

Fu et al. (Nov. 1999) "A microfabricated fluorescence-activated cell sorter," *Nature Biotechnology*, 17:1109-1111 [© 1999 Nature America Inc. http://biotech.nature.com].

Fu et al., (Jun. 1, 2002) "An integrated microfabricated cell sorter," *Analytical Chemistry*, 74(11):2451-2457.

Godin et al., (2008) "Microfluidics and photonics for Bio-System-on-a-Chip: A review of advancements in technology towards a microfluidic flow cytometry chip," *J. Biophoton.*, 1(5):355-376. [DOI 10.1002/jbio.200810018].

He et al., (2005) "Selective Encapsulation of Single Cells and Subcellular Organelles into Picoliter- and Femtoliter—Volume Droplets," *Analytical Chemistry*, 77(6):1539-1544.

Hellman et al. (Jun. 15, 2007) "Laser-Induced Mixing in Microfluidic Channels," *Analytical Chemistry*, 79(12):4484-4492.

Hessel et al., (2004) *Chemical Micro Process Engineering: Modelling and Reactions*, New York: Wiley-VCH Verlag GmbH & Co. KGaA, Weinheim, 36 pages.

Ho et al., (2005) "Micromachined electrochemical T-switches for cell sorting applications," *Lab on a Chip*, 5:1248-1258. [Downloaded by University of California—Los Angeles on Apr. 18, 2013 19:05:23. Published on Sep. 21, 2005 on http://pubs.rsc.org | doi:10.1039/B507575K].

Holmes et al., (2007) "Bead-based immunoassays using a micro-chip flow cytometer," *Lab on a Chip*, 7:1048-1056. [Downloaded by University of California—Los Angeles on Apr. 18, 2013 19:09:02. Published on Jun. 14, 2007 on http://pubs.rsc.org | doi:10.1039/B707507N].

Hsiung et al., (2006) "Micro-droplet formation utilizing microfluidic flow focusing and controllable moving-wall chopping techniques," *J. Micromechanics and Microengineering*, 16:2403-2410 [Downloaded on Apr. 18, 2013 at 19:11, http://iopscience.iop.org/0960-1317/16/11/022].

Huang et al., (2006) Cancer Cell Imaging and Photothermal Therapy in the Near-Infrared Region by Using Gold Nanorods, *J. Am. Chemical Society*, 128:2115-2120.

Huh, et al. (2003) "Reversible Switching of High-Speed Air-Liquid Two-Phase Flows Using Electrowetting-Assisted Flow-Pattern Change," *JACS*, 125:14678-14679.

Hur et al., (2012) "Sheathless inertial cell ordering for extreme throughput flow cytometry," *Lab on a Chip*, 10:274-280. [Downloaded by University of California—Los Angeles on Apr. 18, 2013 19:12:27. Published on Dec. 18, 2009 on http://pubs.rsc.org | doi:10.1039/B919495A].

Ibrahim et al., (2003) "High-speed cell sorting: fundamentals and recent advances," *Current Opinion in Biotechnology* 14(1):5-12.

Idota et al., (2005) "Microfluidic Valves Comprising Nanolayered Thermoresponsive Polymer-Grafted Capillaries," *Advanced Materials*, 17:2723-2727.

Irimia, Daniel and Toner, Mehmet (Mar. 2006) "Cell handling using microstructured membranes," *Lab on a Chip*, 6:345-352. [Downloaded by University of California—Los Angeles on Apr. 18, 2013 19:10:43. Published on Feb. 8, 2006 on http://pubs.rsc.org | doi:10.1039/B515983K].

Jensen, K. (Jun. 25, 1998) "Chemical kinetics—Smaller, faster chemistry," *Nature*, 393:735-737.

Jensen, K.F. (Jan. 2001) "Microreaction engineering—is small better?" *Chemical Engineering Science*, 56:293-303.

Kim et al., (Jul. 2007) "Novel platform for minimizing cell loss on separation process: Droplet-based magnetically activated cell separator," *Review of Scientific Instruments*, 78:074301-1-7.

Leary, James F., (2005) "Ultra high-speed sorting," *International Society for Analytical Cytology, Cytometry Part A* 67A:76-85.

Li et al., (2011) "Fast on-demand droplet fusion using transient cavitation bubbles," *Lap on a Chip*, 11:1879-1885 [Published on Apr. 12, 2011. Downloaded by Korea Advanced Institute of Science & Technology / KAIST on Jan. 11, 2013 00:55:20.].

Marcus et al., (May 1, 2006) "Microfluidic single-cell mRNA isolation and analysis," *Analytical Chemistry*, 78(9):3084-3089.

Mehta et al., (Jan. 5-8, 2009) "Magnetic Nanowire-Enhanced Optomagnetic Tweezers," Proceeding of the 2009 4th IEEE International Conference on Nano/Micro Engineered and Molecular Systems, Shenzhen, China, pp. 1004-1007.

Melin et al., (2007) "Microfluidic Large-Scale Integration: The Evolution of Design Rules for Biological Automation," *Annual Review of Biophysics and Biomolecular Structure*, 36:213-231. [Annu. Rev. Biophys. Biomol. Struct. 2007.36:213-231. Downloaded from www.annualreviews.org by University of California—Los Angeles—Law Library UCLA on Apr. 18, 2013. For personal use only.].

Panaro et al., (Feb. 2005) "Micropillar array chip for integrated white blood cell isolation and PCR," *Biomolecular Engineering*, 21:157-162.

Park et al., (2010) "A pulse laser-driven microfluidic device for ultra-fast droplet generation on demand and single-cells encapsulation," *14th International Conference on Miniaturized Systems for Chemistry and Life Sciences*, Groningen, The Netherlands, pp. 2129-2131.

Park et al., (2011) "High-speed droplet generation on demand driven by pulse laser-induced cavitation," *Lab on a Chip*, 11:1010-1012.

(56) References Cited

OTHER PUBLICATIONS

Pitsillides et al., (Jun. 2003) "Selective cell targeting with light-absorbing microparticles and nanoparticles," *Biophys J*, 84(6):4023-32.

Shirasaki et al., (Feb. 1, 2006) "On-Chip Cell Sorting System Using Laser-Induced Heating of a Thermoreversible Gelation Polymer to Control flow," *Analytical Chemistry* 78(3):695-701.

Sun et al., (2007) "Design, simulation and experiment of electroosmotic microfluidic chip for cell sorting," *Sens. Actuators A.* 133(2):340-348.

Vogel et al. (Dec. 2005) "Mechanisms of femtosecond laser nanosurgery of cells and tissues," *Applied Physics B-Lasers and Optics*, 81:1015-1047.

Wang et al., (2007) "High-density microfluidic arrays for cell cytotoxicity analysis," *Lab on a Chip*, 7:740-745. [Downloaded by University of California—Los Angeles on Apr. 18, 2013 19:50:05. Published on Apr. 4, 2007 on http://pubs.rsc.org | doi:10.1039/B618734J].

Wang et al., (Jan. 2005) "Microfluidic sorting of mammalian cells by optical force switching," *Nature Biotechnology*, 23(1):83-87.

Wu et al., (Jan. 18, 2010) "Image patterned molecular delivery into live cells using gold particle coated substrates," *Optics Express*, 18(2):938-946.

Wu et al., (2012) "Pulsed laser triggered high speed microfluidic fluorescence activated cell sorter," *Lab on a Chip* 12:1378-1383 [Downloaded by University of California—Los Angeles on Apr. 18, 2013 19:33:06. Published on Feb. 15, 2012 on http://pubs.rsc.org | doi:10.1039/C2LC21084C].

Wu et al., (Oct. 6, 2008) "Pulsed laser triggered high speed microfluidic switch," *Appl. Phys. Lett.* 93, 144102. [Downloaded Oct. 10, 2008 to 131.252.222.209. Redistribution subject to AIP license or copyright; see http://apl.aip.org/apl/copyright.jsp].

Xu, Jie and Attinger, Daniel, (2008) "Drop on demand in a microfluidic chip" *J. Micromechanics and Microengineering*, 18:065020, 11 pp [downloaded on Apr. 18, 2013 at 19:43, http://iopscience.iop.org/0960-1317/18/6/065020].

Yao et al., (Nov./Dec. 2005) "Elevation of plasma membrane permeability by laser irradiation of selectively bound nanoparticles," *J Biomed Opt*, 10(6):064012-1-064012-8.

Yoshida et al., (Mar. 2005) "Enhancement of Chemical Selectivity by Microreactors," *Chemical Engineering & Technology*, 28(3):259-266.

Zeng et al., (2009) "Microvalve-actuated precise control of individual droplets in microfluidic devices" *Lab on a Chip*, 9:1340-1343 [Downloaded by University of California—Los Angeles on Apr. 18, 2013 19:50:54. Published on Mar. 27, 2009 on http://pubs.rsc.org | doi:10.1039/B821803J].

Zhong et al., (2008) "A microfluidic processor for gene expression profiling of single human embryonic stem cells," *Lab on a Chip*, 8:68-74. [Downloaded on Apr. 18, 2013 19:20:57. Published on Nov. 2, 2007 on http://pubs.rsc.org | doi:10.1039/B712116D].

Zhong et al., (2008) "Microfluidic Devices for Investigating Stem Cell Gene Regulation via Single-Cell Analysis," *Current Medicinal Chemistry*, 15(28):2897-2900.

U.S. Final Office Action dated Aug. 20, 2014 issued in U.S. Appl. No. 13/370,196.

PCT International Preliminary Report on Patentability dated Aug. 12, 2014 issued in PCT/US2013/025434.

U.S. Appl. No. 14/930,054, Nov. 2, 2015, Chiou et al.

U.S. Advisory Action dated Mar. 5, 2015 issued in U.S. Appl. No. 13/370,196.

U.S. Notice of Allowance dated Jun. 5, 2015 issued in U.S. Appl. No. 13/370,196.

U.S. Notice of Allowance dated Jun. 24, 2015 issued in U.S. Appl. No. 13/370,196.

Australian Patent Examination Report No. 1 dated Sep. 15, 2015 issued in AU 2013216804.

Chinese Office Action (no translation) dated Jul. 24, 2015 issued in CN 201380016299.3.

European Extended Search Report dated Jan. 7, 2016 issued in EP 13 74 6888.

Li et al. (2010) "Two Same-Sized Droplets Coalescence by Laser-Induced Cavitation Bubbles," *14th International Conference on Miniaturized Systems for Chemistry and Life Sciences*, Oct. 3-7, 2010, Groningen, The Netherlands, pp. 1088-1090.

Tandiono et al. (2010) "Creation of cavitation activity in a microfluidic device through acoustically driven capillary waves," *Lab Chip*, 10:1848-1855.

Zwaan et al. (2007) "Controlled cavitation in microfluidics," *Phys. Rev. Lett.* 98:2545, 4 pages.

\* cited by examiner

PULSED LASER TRIGGERED HIGH SPEED MICROFLUIDIC SWITCH AND APPLICATIONS IN FLUORESCENT ACTIVATED CELL SORTING

CROSS-REFERENCE TO RELATED APPLICATIONS

This application claims benefit of and priority to U.S. Ser. No. 61/232,416, filed Aug. 8, 2009which is incorporated herein by reference in its entirety for all purposes.

STATEMENT OF GOVERNMENTAL SUPPORT

This invention was made with Government support under Grant No. NCC2-1364, awarded by the National Aeronautics & Space Administration and under Grant No. EY018228, awarded by the National Institute of Health and Grant No. 0747950, 0852701, 0901154, awarded by the National Science Foundation. The Government has certain rights in the invention.

FIELD OF THE INVENTION

The present invention relates to the field of microfluidics. In certain embodiments a pulsed laser triggered high speed microfluidic switch is provided.

BACKGROUND

Benchtop flow cytometers are the current standard for high speed, multi-parametric cell sorting. However, these droplet-based sorting systems are often open and have several intrinsic drawbacks. Contamination from the environment, operators, and samples are major issues for downstream cell culture and analysis. Cell loss during transfer is also hard to prevent. In addition, infectious samples need to be treated with extreme caution because droplet-based sorting mechanisms generate biohazardous aerosols.

Microfluidic approaches have the potential to solve these issues by providing a sorting system on a disposable chip to enclose all cells and liquids in a closed, safe, and sterile environment. This eliminates the need for vacuum containment systems and facility additions to protect operators against aerosolized pathogen exposure in conventional droplet-based fluorescence activated cell sorting (FACS). Furthermore, a microfluidic approach is advantageous for handling small numbers of cells (100-100,000) with high yield, which is difficult to achieve with conventional FACS. This feature is particularly beneficial in applications involving precious cells, such as primary cells that cannot be expanded to large populations. In addition, other lab-on-a-chip devices, the potential exists for further functionality integrated on-chip, such as sample preparation, cell incubation, chemical analysis, PCR, or other assays of the sorted populations. Specifically, these capabilities would enable sorting and molecular analysis of rare cells in blood such as circulating tumor cells (CTCs), providing powerful molecular diagnostic information concerning cancer drug resistance in a non-invasive manner for personalized therapies.

Although a variety of different physical on-chip switch mechanisms have been proposed, none has simultaneously satisfied the requirements of high throughput, purity, and recovery of live, unstressed mammalian cells (see, e.g., Applegate et al. (2006) *Lab on a Chip*, 6: 422-426; Fu et al. (2002) *Analytical Chem.*, 74: 2451-2457; Fu et al. (1999) *Nature Biotechnology*, 17: 1109-1111; Ho et al. (2005) *Lab on a Chip*, 5: 1248-1258; Holmes et al. (2007) *Lab on a Chip* 7: 1048-1056; Idota et al. (2005) *Advanced Materials*, 17: 2723-; Kim et al. (2007) *Rev. Sci. Inst.*, 78(7): 074301.; Shirasaki et al. (2006) *Analyt. Chem.*, 78: 695-701; Wang et al. (2005) *Nature Biotechnol.*, 2383-8237). Some of the first demonstrations of the sorting of bacterial cells relied on electrokinetic mobilization of fluid through a microfluidic network, achieving rates of 1-20 cells/sec. Unfortunately, this method is limited by the difficulty of maintaining cell viability under high electric fields, particularly for eukaryotic cells, and by buffer incompatibilities. Hydrodynamic flow control based on either on-chip or off-chip fluidic valves has been demonstrated for sorting living cells; in this case, preserving cell viability is less of a problem. However, because of the slow pneumatic mechanical switch and the relatively large volume of fluid displaced in every switch cycle, cell sorting demonstrations using hydrodynamic switching are slow. The recently demonstrated PZT method (Cho et al. (2010) *Lab on a Chip*, 10: 1567-1573) is able to achieve 1000 cells/sec. However, this sorting speed is still 1~2 orders of magnitude slower than commercial FACS.

SUMMARY OF THE INVENTION

A novel and ultrafast microfluidic switching mechanism is described herein. Driven by laser pulse induced cavitation bubbles the switching mechanism permits the fabrication of microfluidic fluorescence activated cell sorters (FACS) capable of sorting at a speeds higher than 10,000 cells/sec. The sorters can be fabricated using monolayer PDMS channels to operate and no mechanical pumps and valves are required for the sorting function. This provides excellent compatibility with standard PDMS based microfluidic chips or platforms that have been widely applied in the past ten years for advancing various fields in biology [11-16].

Accordingly, in various embodiments, a microfluidic switch, and a new type of fluorescent activated cell sorter (FACs) is provided herein. The FACs described herein can be provided as a standard microfluidic modules that users can add on when they order microfluidic chips from a foundry service for complex and multistep downstream analysis. Methods of using the high speed switch, a FACs comprising one or more such switches, and various analytic, and other, systems comprising such switches are provided herein.

In certain embodiments this invention provides a pulsed-laser triggered microfluidic switching mechanism that can achieve a switching time of 70 μs, or even shorter by using a harder microfluidic PDMS (or other flexible/elastic) channel. The switching mechanism permits the fabrication of FACS capable of sorting at a speed higher than 10,000 cells/sec. This switching speed is two orders of magnitude shorter than that of the fastest switching mechanism utilized in previous μFACS.

In certain embodiments a high-speed microfluidic switch or a device comprising such a switch is provided, where the switch typically comprises a first microfluidic channel comprising a bifurcation into two or more paths, the two or more paths comprising at least a first path and a second path; and a chamber or second channel adjacent to the bifurcation disposed such that formation of a gas or plasma bubble in the chamber or adjacent channel redirects particles flowing into the first path so they flow into the second path. In certain embodiments the switch further comprises a port, a wall, or a channel, or a nozzle between the chamber or second channel and the first channel. In certain embodiments the switch further comprises a wall between the between the chamber or second channel and the first channel where the wall is disposed so that formation of a gas or plasma bubble in the chamber or adjacent channel deforms the wall of the first microfluidic channel to redirect particles flowing into the first path so they flow into the second path.

In certain embodiments a high-speed microfluidic switch or a device comprising such a switch is provided, where the switch typically comprises a first microfluidic channel comprising a bifurcation into two or more paths, the two or more paths comprising at least a first path and a second path; a chamber or second microfluidic channel adjacent to the first microfluidic channel; a connecting port or channel connecting the chamber or microfluid channel to the first microfluidic channel; and a third channel or chamber adjacent to the chamber or second microfluidic channel disposed such that the formation of a bubble in the third channel or chamber induces a fluid flow or pressure through the connecting port or channel that redirects particles flowing into the first path so they flow into the second path. In various embodiments described herein the first microfluidic channel is a Y-shaped microchannel. In various embodiments described herein the first microfluidic channel is formed from an elastomeric material (e.g., polydimethylsiloxane (PDMS), acryloxy perfluoropolyether (a-PFPE), polyurethane (PU), amorphous fluoropolymer, and the like). In certain embodiments the switch has a switching time of less than about 100 μsec, or less than about 70 μsec, or less than about 60 μsec, or less than about 50 μsec. In certain embodiments the switch is present in a system comprising an energy source (e.g., laser, microwave emitter, ultrasonic emitter, electrical heater, etc.) capable of forming a bubble in the chamber or adjacent channel. In certain embodiments vapor bubbles (e.g., laser-excited vapor bubbles) are excited in the main sample channel, or the middle channel with a nozzle opening. In various embodiments the vapor bubbles are excited in a liquid medium, gel medium, or photoreactive polymer medium. In certain embodiments the liquid or gel comprises a dye or light-absorbing nano/microparticles (e.g. dye molecules, metal nanoparticles). In certain embodiments the switch is disposed on a substrate comprising a material selected from the group consisting of a polymer, a plastic, a glass, a quartz, a dielectric material, silicon, germanium, ceramic, or a metal. In certain embodiments the switch is integrated with other microfluidic components (e.g., sample application ports or chambers, filters, channels, wells valves, and the like). In certain embodiments the switch is a component of a lab-on-a-chip. In certain embodiments the switch is a component of a cell sorter.

In various embodiments systems are provided for controlling microfluidic flow. In certain embodiments the system comprises a switch as described herein and an excitation source for forming gas bubbles in a fluid or gel. In certain embodiments the excitation source is a laser, a microwave source, an ultrasonic energy source, an electrical heater, a non-coherent optical source, and the like. In certain embodiments the system further comprises components for detecting particles or cells in the system.

In various embodiments methods are provided for detecting or sorting particles or cells. In various embodiments The methods typically involve flowing the particle or cells through a switch according as described herein and activating the switch to channel desired particles into a desired flow path.

In various embodiments the switches described herein are used in cell detection/sorting systems and methods (e.g., μFACS). In various embodiments cell detection is based on fluorescent (optical) signals and can utilize scattering signals for particle shape and size analysis, and the like. In various embodiments fluorescent excitation light sources can be laser, LED, or halogen lamps, and the like. In various embodiments PMT, APD, or CCD or CMOS camera, and the like can be used for cell or particle detection and analysis.

In certain embodiments two or more μFACS can be connected in sequence for constructing cascade μFACS for parallel single cell analyses.

Illustrative, sorted samples include, but are not limited to, cells, particles, immiscible droplets and molecules. In various embodiments the sorted particles range from few mm (stem cell colony) to ~1 nm (e.g., single molecule).

DETAILED DESCRIPTION

In certain embodiments a device is provided to achieve high speed flow switching in a microfluidic channel. The switching mechanism is realized by exciting dynamic vapor bubbles with focused laser (or other energy) pulses in a microfluidic channel. The rapid formation of a "cavitation" bubble in a microchannel acts to displace objects (e.g., particles or cells) flowing through the microchannel directing them to particular locations. A microfluidic channel or microchannel refers to a channel (open or closed top) having one or more characteristic dimensions (e.g., height, width, diameter) of a submillimeter scale. In certain embodiments the channel width and/or height is typically less than about 500 μm, more preferably less than about 300 μm.

Figure 1A:
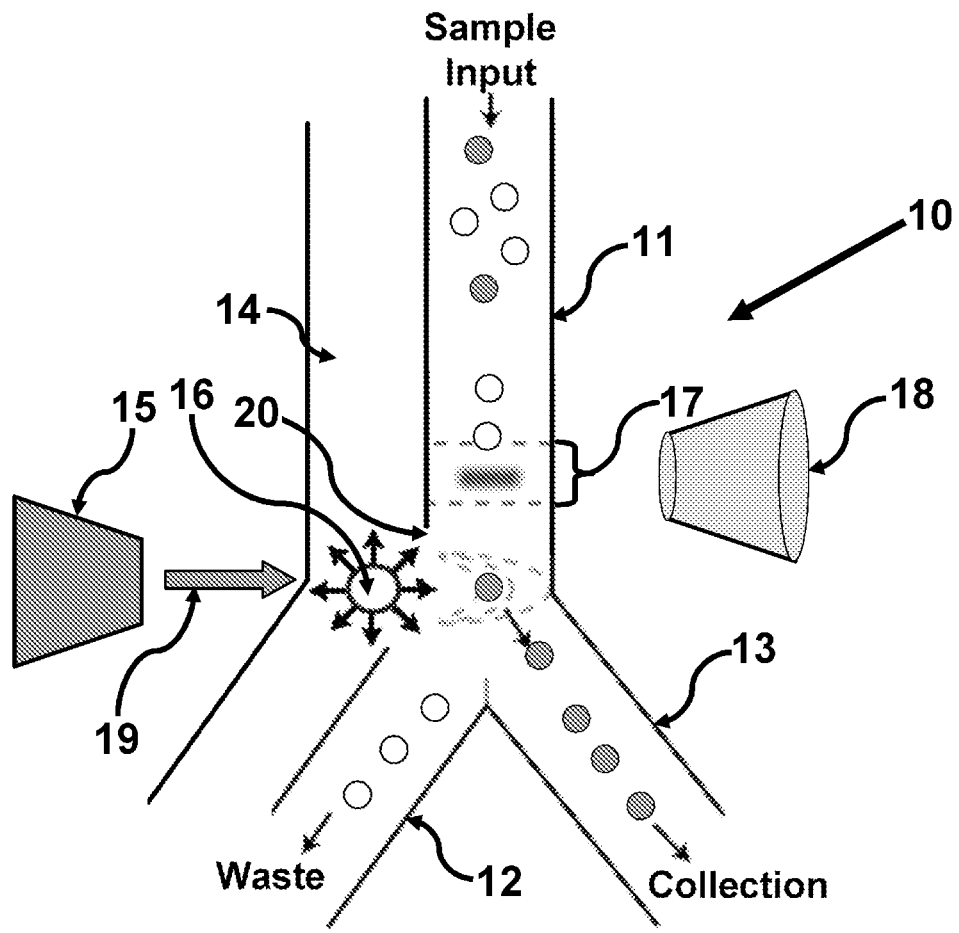
FIGS. 1A and 1B schematically illustrate two embodiments of a high-speed microfluidic switch.

One illustrative embodiment is schematically shown in FIG. 1A. As illustrated in this figure, a high-speed microfluidic switch 10 comprises a first microfluidic channel 11 into two or more paths, e.g., a first path 12 and a second path 13. A second channel or chamber 14 is located adjacent to, or in proximity to, the bifurcation and disposed such that formation of a gas or plasma bubble 16 in the chamber or channel 14 redirects particles flowing into the first path 12 so they flow into the second path 13. A laser pulse) or other energy pulse 19 produced by an energy source 15 is focused on the medium inside the second channel or chamber 14. The intense energy field generates a heated gas or plasma within the focal volume. The heat dissipates into the surrounding liquid and induces the formation of one or more cavitation bubbles 16. The expanding cavitation bubble redirects particles from the first path 12 to the second path 13. The rapid bubble formation/expansion acts as a mechanical switch to alter the flow pattern in the adjacent microfluidic channel.

In certain embodiments the switch further comprises a detector 18 that determines when a target (e.g., labeled particle or cell) enters an analysis region 17 and activates the energy source to direct the target particle(s) or cell(s) into the second path 13.

Figure 1B:
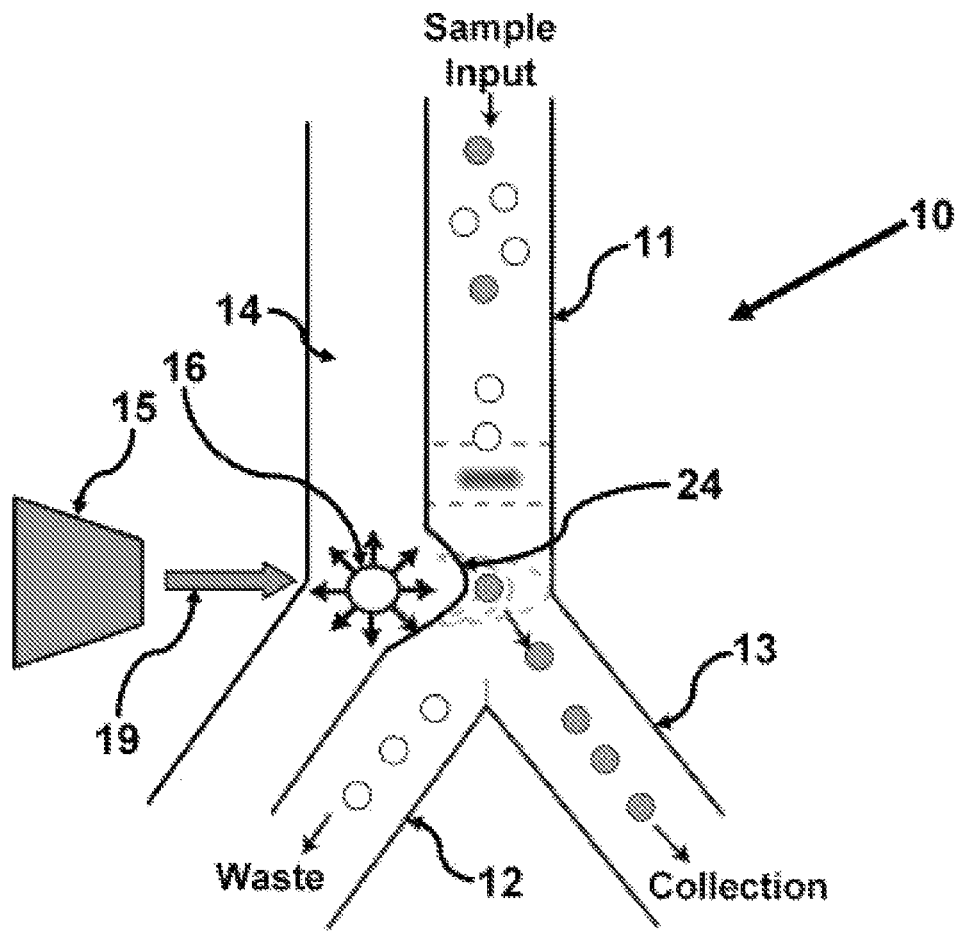

In certain embodiments, the second channel or chamber 14 is in fluid communication with the first microfluid channel 11 by a gap, channel, or port 20. In certain embodiments, as schematically illustrated in FIG. 1B the second channel or chamber 14 is separated from the first microfluidic channel (microchannel) by a channel wall 24, or by an intervening third channel or chamber. As illustrated in FIG. 1B formation of the gas or plasma bubble deflects the channel wall 24 thereby redirecting particles into the second channel 13. It will be appreciated that the speed of the switch can be controlled, in part, by the stiffness of the wall 24.

Figure 2:
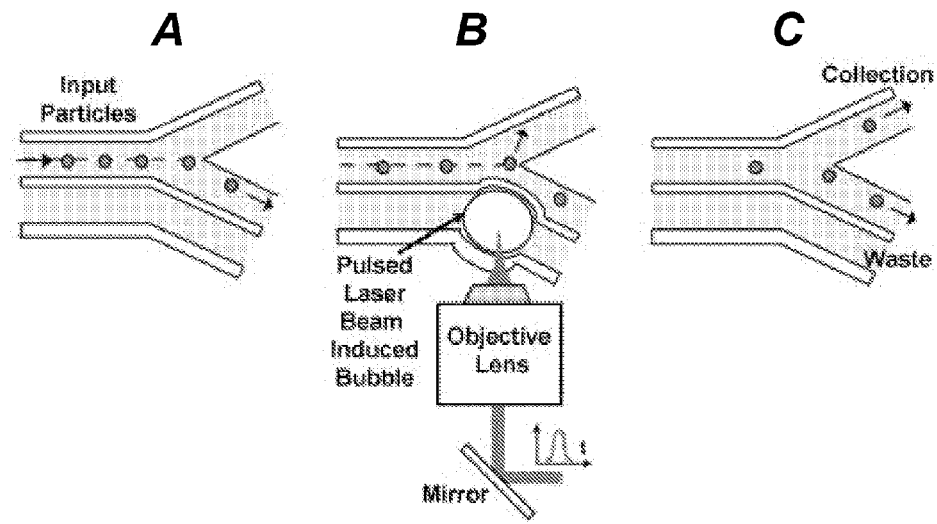
FIG. 2 illustrates a schematic of a pulsed laser triggered microfluidic switch. (A) Before (B) during and (C) after switching.

FIG. 2, panels A-C, show a schematic of the operation of one embodiment of the pulsed laser triggered microfluidic switch. As illustrated in this figure, device consists of a Y-shaped microchannel with two outlets, collection and waste. Using hydrodynamic focusing, the input particles or cells are focused slightly off the centerline of the main channel and go into the waste channel after the Y junction. Separated by a thin wall, another channel runs in parallel with the waste channel. This channel is positioned above the objective lens, which focuses the laser pulse to induce optical breakdown of the liquid medium and the subsequent cavitation bubble. As the bubble expands, the channel wall, being elastic, is deformed and squeezes the waste channel on the opposite side. This transient deformation of the channel wall alters the flow pattern in the main channel. A particle or cell approaching the fork of the Y junction is thus switched to flow in the collection channel.

Figure 3:
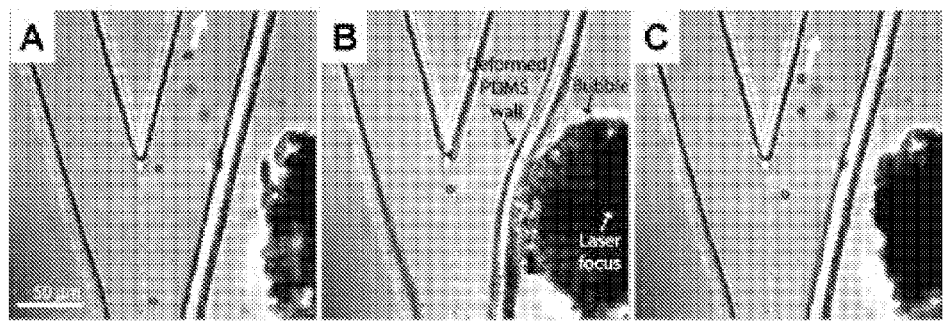
FIG. 3, panels A-C show transient change of particle flow pattern in the microchannel due to a pulsed-laser induced bubble. Panel A: Particle flow without laser pulses. Panel B: 400 ns after the laser pulse. Panel C: 1 s after the laser pulse.
Figure 4:
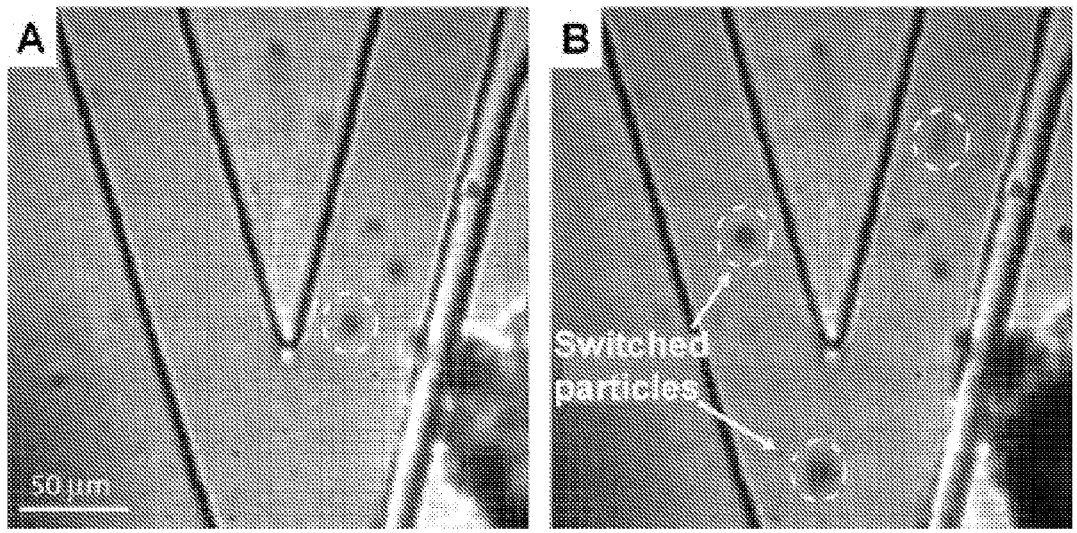
FIG. 4, panels A and B illustrate particle switching triggered by a pulsed laser microbeam. Panel A: Before switching. Panel B: 250 μs after the laser pulse.

A time series showing the action of the switch is schematically illustrated in FIG. 2, panels A-C and is shown in the photographs presented in FIG. 3, panels A-C, and in FIG. 4, panels A and B.

Figure 5:
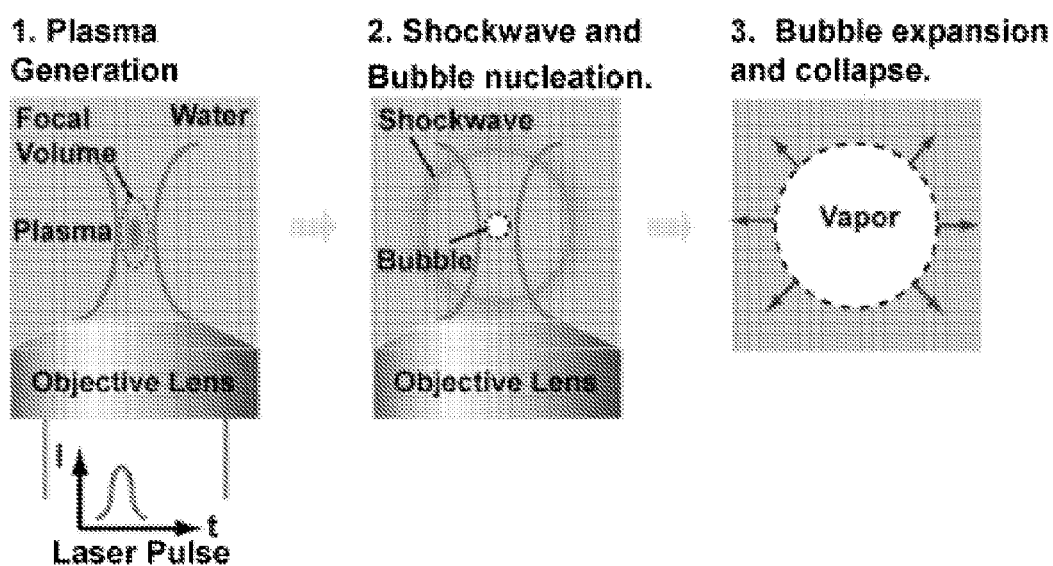
FIG. 5 illustrates laser-induced bubble formation in water.

The rapidly expanding gas/vapor/plasma bubble (illustrated in FIG. 5) can be triggered in a few nanoseconds to actuate surrounding fluid and objects including cells. In certain embodiments the bubble expansion speed can be up to 100 m/sec. By controlling the pulse energy and induced bubble size, the lifetime of a full cycle of cavitation can be controlled to be less than 1 μsec.

In addition, the bubble size can be tuned to a volume of less than one nanoliter. The feature of 3D optical focusing allows accurately addressing this small fluid perturbation close enough to a cell to effectively switching it into a collection channel without damaging it. The small perturbation volume and short perturbation time allows fast recovery from a switching event, which is an important parameter for high speed cell sorting in closed channel systems.

One advantage of the devices described herein is the rapid switching time far surpassing other microfluidic switches reported. The switching mechanism, which is based on bubble expansion and in certain embodiments deforming and restoring of the channel wall, takes place on the time scale of few microseconds to tens of microseconds, depending on the bubble size, pulsed channel dimensions and the channel wall thickness and material. Moreover, where a channel wall is present, the switched particles/cells are shielded from the direct impact of the explosive expansion and collapse of the pulsed-laser induced bubble. The completely isolated bubble excitation and cell channels allow cells being switched in a friendly environment without the need to expose to low ionic buffers such as in the cases of electrokinetic sorting or strong optical fields in the case of optical sorting. This way minimum electrical, optical, ionic, and chemical stresses are exerted on the cells during switching, and a high level of sample integrity and viability can be maintained. The cells are purely sorted by mechanical fluidic forces. This device has the potential to achieve high-speed and high-viability sorting on fragile and rare biological cells. This switching mechanism is fully compatible with widely applied PDMS based microfluidic lab-on-a-chip systems for subsequent analysis after cell sorting.

Figure 6:
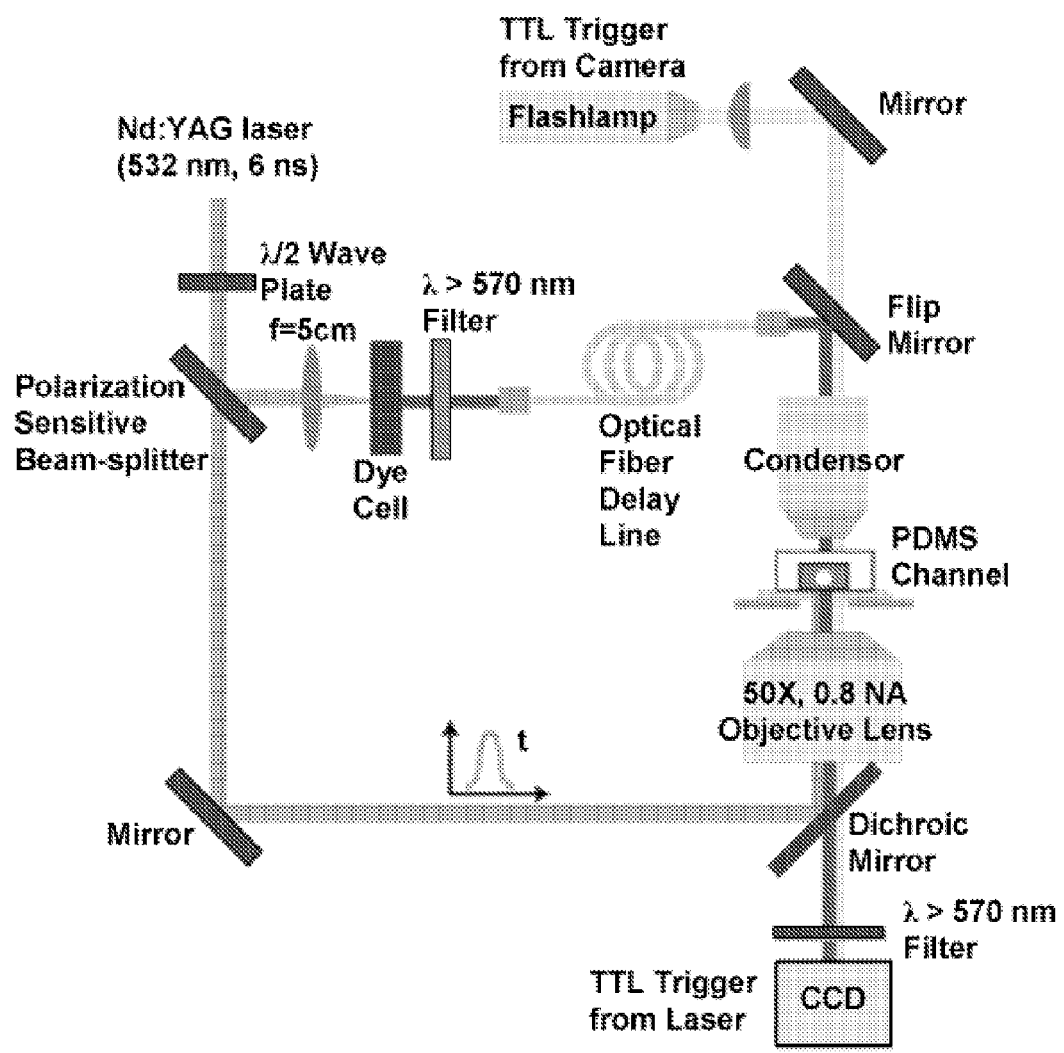
FIG. 6 schematically illustrates a time-resolved imaging system. The system is capable of capturing the full dynamics of cavitation bubble formation and growth over a timescale from nanoseconds to hundreds of microseconds.
Figure 7A:
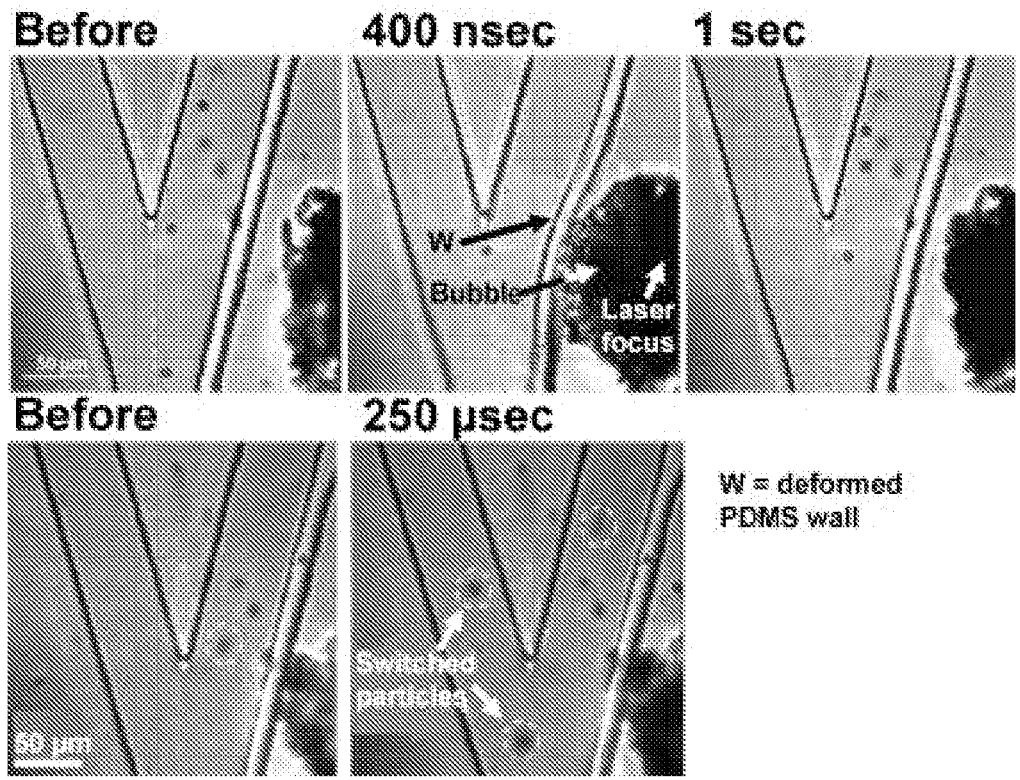
FIG. 7A shows photographs of particle switching in a pulsed laser triggered microfluidic switch.
Figure 7B:
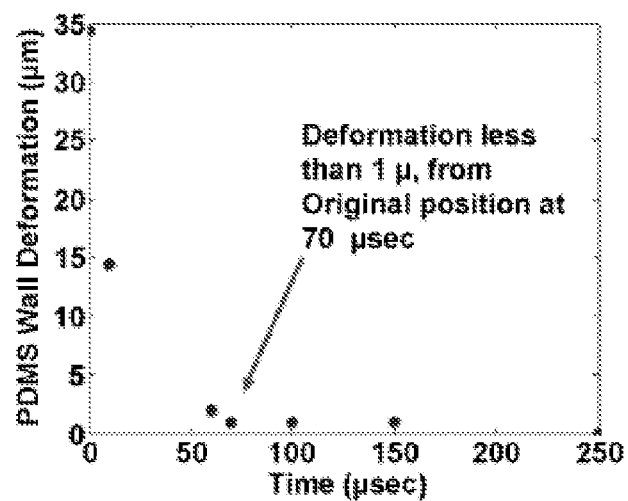
FIG. 7B shows microchannel wall deformation as a function of time.

A time-resolved imaging system (see, e.g., FIG. 6) has been constructed to capture the nanosecond transient channel wall deformation and the particle flow pattern. We have demonstrated a switching time of 70 μsec in our device (see, e.g., FIG. 7B). The demonstration was done by switching polystyrene microspheres (7 μm in diameter) in a Y channel (see, e.g., FIG. 7A). This proof-of-concept demonstration has confirmed the feasibility of using laser excited bubbles for developing ultrafast μFACS devices.

Figure 8:
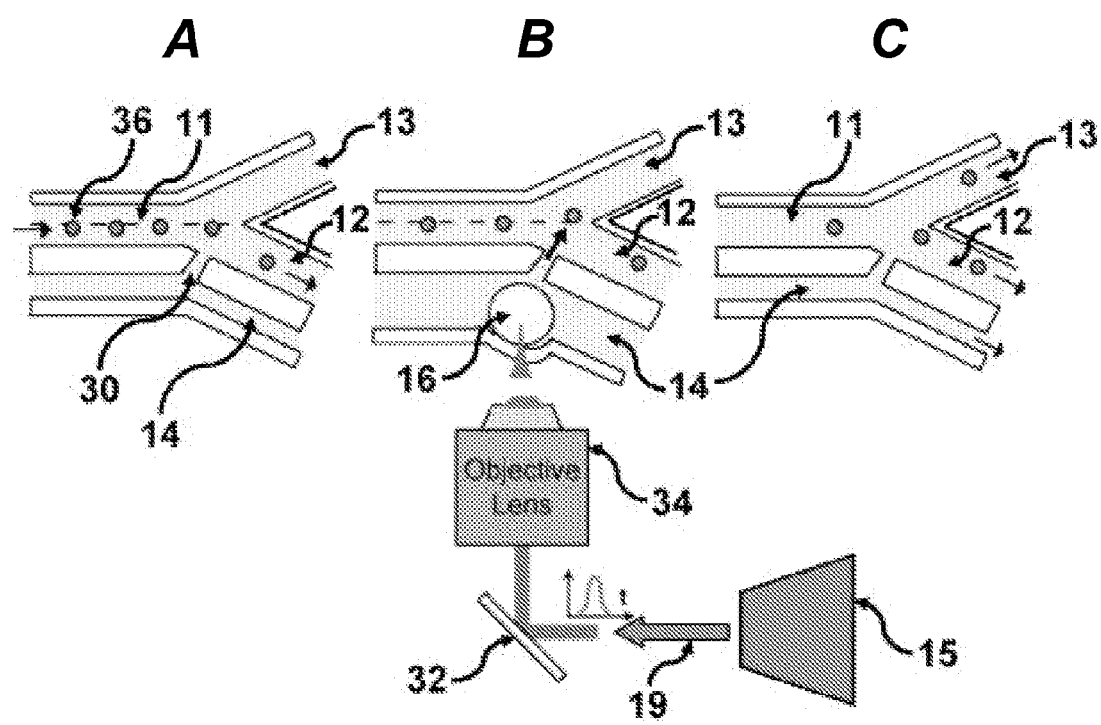
FIG. 8 schematically illustrates an embodiment of the microfluidic switch that incorporates a nozzle.
Figure 9:
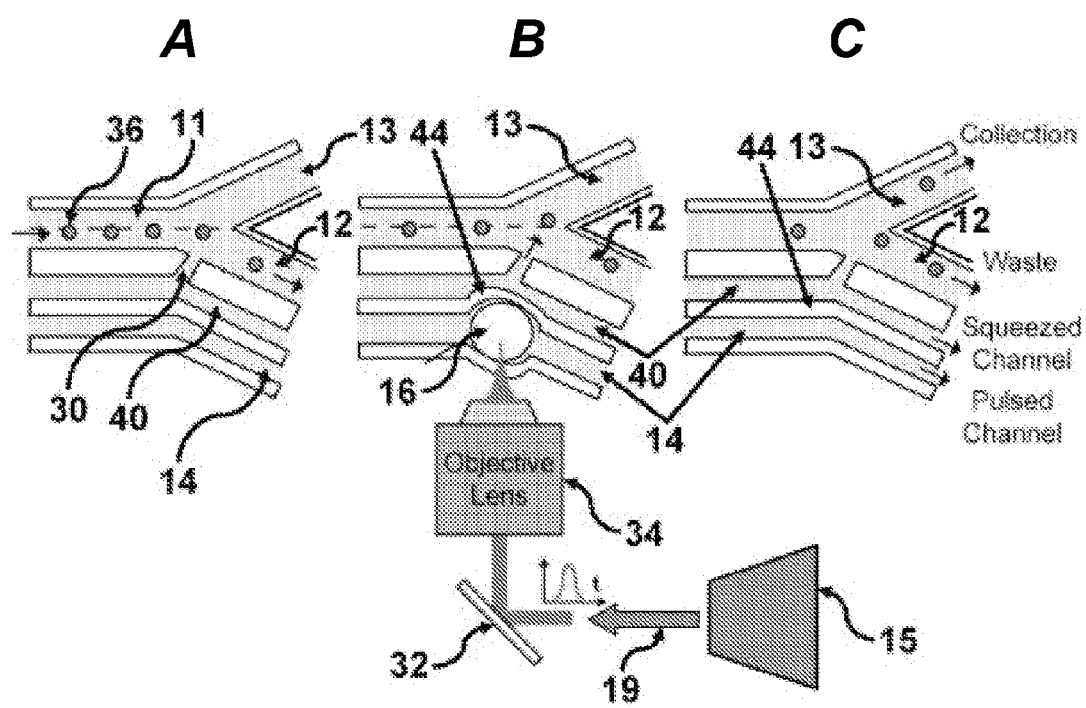
FIG. 9 schematically illustrates an embodiment of the microfluidic switch that incorporates a nozzle and a third microchannel or chamber.

In an embodiment schematically illustrated in FIG. 8, panels A-C, a liquid jet-forming nozzle 30 is introduced into the microfluidic structure. As illustrated in this figure, the nozzle 30 connects the second channel or chamber 14 is to the first channel 11. Using hydrodynamic focusing, or other techniques, the input particles or cells 36 are focused slightly off the centerline of the main channel (first microchannel) 11 and go into the waste channel (first path) 12 (see, e.g., panel A). As illustrated in panel B, an energy pulse 19 (e.g., a laser pulse) produced by energy source 15 is directed via a mirror 32 into a lens or lens system 34 to focus the energy into the second chamber or channel 14 thereby producing expanding bubble 16. The expanding bubble forces fluid through the nozzle 30 forming a jet that deflects particles/cells 36 into second path 13 (e.g., a collection channel). In this design, the switching window (area over which switching occurs) is reduced to tens of microns in diameter, depending on the size of the nozzle opening. This corresponds to a factor of 10 reduction of the switching window size. A smaller switching window allows for shorter distance between adjacent samples in the microfluidic stream, and in turn higher device throughput by switching more samples within a given amount of time.

In another embodiment, schematically illustrated in Figure a third chamber or channel 40 is disposed between the first microchannel 11 and the second microchannel 14. As illustrated in the figure, a wall 44 separates the third chamber or channel 40 from the second chamber or channel 14 (although in certain embodiments a port or gap may be present). A nozzle 30 connects the third chamber or channel 40 to the first microchannel 11. Using hydrodynamic focusing, or other techniques, the input particles or cells 36 are focused slightly off the centerline of the main channel (first microchannel) 11 and go into the waste channel (first path) 12 (see, e.g., panel A). As illustrated in panel B, an energy pulse 19 (e.g., a laser pulse) produced by energy source 15 is directed via a mirror 32 into a lens or lens system 34 to focus the energy into the second chamber or channel 14 thereby producing expanding bubble 16. As the bubble expands, the channel wall 44, being elastic, is deformed and squeezes the squeezed channel 40 on the opposite side. This transient deformation of the channel wall forces the liquid to pass through the nozzle 30 and deflects the particle 36 towards the second path 13 (e.g., collection outlet)

While nozzle 30 is shown in fluid communication with between the second or third a microchannel or chamber and the first microchannel 11, in certain embodiments, the nozzle is closed by a thinner section of channel wall. The thinner channel wall deflects to a greater degree than the remaining thicker wall thereby producing a local displacement that moves the particles/cells.

Figure 10:
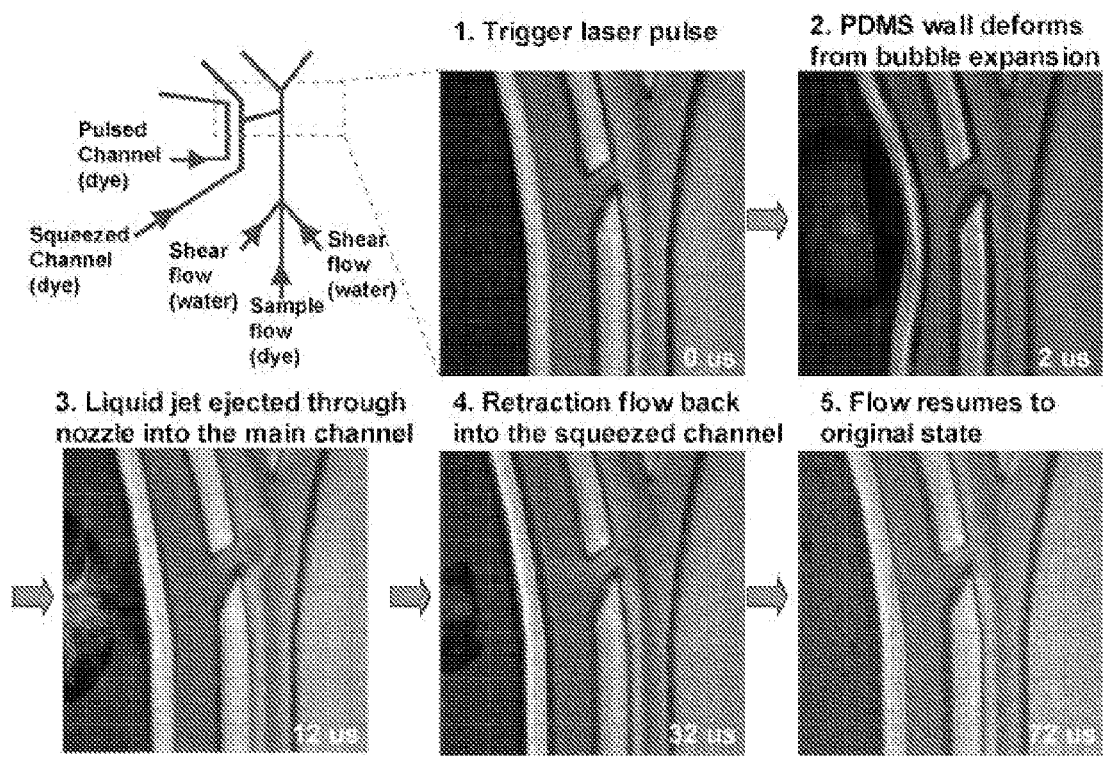
FIG. 10 shows time-resolved images showing the pulsed laser triggered liquid jet deflecting the sample flow (dye) in the main channel.
Figure 11:
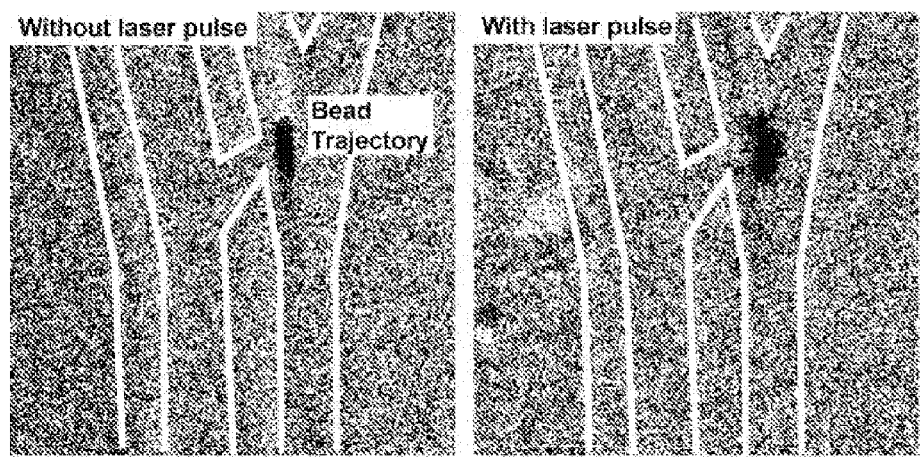
FIG. 11 shows trajectories of 10 μm polystyrene beads. (Left) Without pulsed laser triggered liquid jet, the bead follows the laminar flow streamline towards left outlet. (Right) With pulsed laser triggered liquid jet, the bead was deflected towards right at the nozzle opening.
Figure 12:
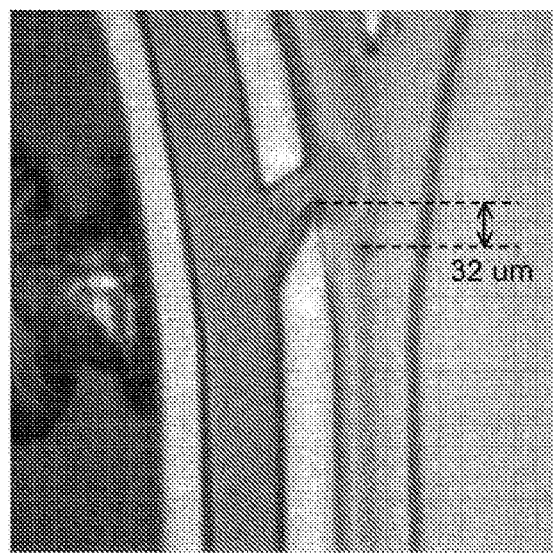
FIG. 12 shows a measured switching window diameter=32 μm.

Photographs illustrating operation of three microchannel configurations are provided in FIGS. 10, 11, and 12. FIG. 10 shows time-resolved images showing the pulsed laser triggered liquid jet deflecting the sample flow (in this case a dye) in the main channel. FIG. 11 shows trajectories of 10 μm polystyrene beads. As shown in the left panel, without pulsed laser triggered liquid jet, the bead follows the laminar flow streamline towards left outlet. As illustrated in the right panel, with pulsed laser triggered liquid jet, the bead was deflected towards right at the nozzle opening. FIG. 12 shows a measured switching window diameter, in this case having a diameter of about 32 μm.

The embodiments described above are illustrative and not intended to be limiting. Using the teachings provided herein other configurations will be available to one of skill in the art. For example, in certain embodiments it is possible to directly excite a bubble in the main sample channel, or the middle channel with a nozzle opening, for particle or cell switching in some cases.

In various embodiments, any of a number of energy sources can be used to excite the formation of a bubble. Such energy sources include, but are not limited to acoustic sources (e.g., ultrasonic transducers), microwave sources, laser sources, and sources of non-coherent optical radiation (e.g., infrared radiation) electrical heating, and the like.

In certain embodiments the energy source 15 is a laser. Lasers are advantageous in that they do not require any electrical or mechanical wiring or interconnects to deliver energy. A laser beam can be focused to any arbitrary 3D location across a transparent substrate. This eliminates the interfacing problems and facilitates the integration on standard foundry microfluidic chips.

Illustrative lasers include, but are not limited to nanosecond pulsed laser with a wavelength at 532 nm. Microsecond, picosecond or femtosecond pulse lasers, and the like, can also be applied In certain embodiments the wavelength of laser can also in the UV, visible light, or near infrared.

In various embodiments the media which the laser excites the bubble in could be liquid (e.g. water, buffer, cell media), a gel, a hydrogel, a photoreactive polymer, or a liquid or gel liquid containing light-absorbing molecules or nano/microparticles (e.g. dye molecules, metal nanoparticles), a gas (e.g., a combustible or noncombustible gas), an oil (or other non-polar liquid), and the like.

Figure 13:
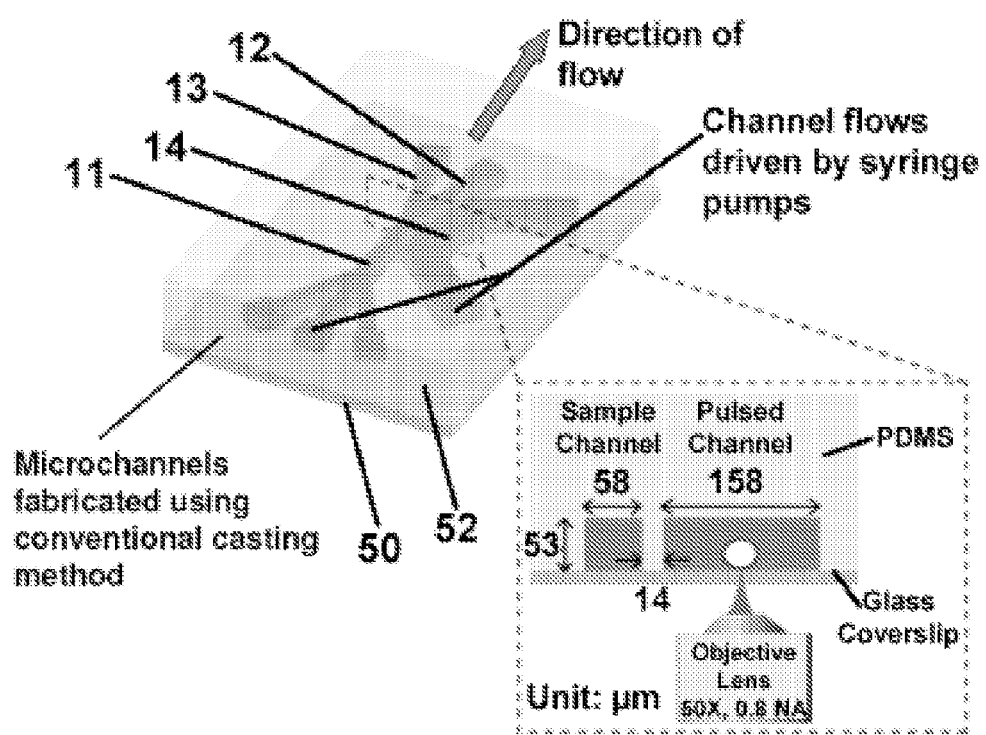
FIG. 13 illustrates the structure of one embodiment of a pulsed laser triggered microfluidic switch fabricated on a substrate 50 out of an elastomeric material 52. As illustrated, the figure shows the first microchannel 11 splitting into a first path 12 and a second path 13. A second microchannel 14 is adjacent to or in proximity to the first microchannel 11.

Typically, although not necessarily, the microchannel switching devices described herein are provided on a substrate that comprises a different material than the material(s) comprising the channels themselves. For example, as illustrated in FIG. 13 the microchannels (e.g., first microchannel 11 splitting into a first path 12 and a second path 13, and second microchannel or chamber 14) can be fabricated in an elastomeric material 52.

In various embodiments, microchannels carrying particles or cells have a characteristic dimension (e.g. height or width or diameter) ranging from about 100 nm or 1 μm up to about 500 μm. In various embodiments the characteristic dimension ranges from about 1, 5, 10, 15, 20, 25, 35, 50, or 100 μm up to about 150, 200, 250, 300, or 400 μm. In certain embodiments the characteristic dimension ranges from about 20, 40, or about 50 μm up to about 100, 125, 150, 175 or 200 μm. In various embodiments the wall thickness between adjacent channels ranges from about 0.1 μm to about 50 μm, ore about 1 μm to about 50 μm, more typically from about 5 μm to about 40 μm. In certain embodiments the wall thickness between adjacent channels ranges from about 5 μm to about 10, 15, 20, or 25 μm.

In various embodiments the channel depth ranges from 5, 10, 15, 20 μm to about 1 mm, 800 μm, 600 μm, 500 μm, 400 μm, 300 μm, 200 μm, 150 μm, 100 μm, 80 μm, 70 μm 60 μm, 50 μm, 40 μm, or about 30 μm. In certain embodiments the channel depth ranges from about 10 μm to about 60 μm, more preferably from about 20 µm to about 40 or 50 µm. In various embodiments the channels can be open or covered.

Where a nozzle is present, in various embodiments, the nozzle diameter ranges from about 0.1 µm, or about 1 µm up to about 300 µm, 200 µm, or about 100 µm, in certain embodiments from about 5, 10, 15, or 20 µm up to about 25, 30, 35, 40, 45, 50, 55, 60, 65, 70, 75, or 80 µm. In certain embodiments the nozzle diameter ranges from about 1, 5, 10, 15 or 20 µm up to about 25, 35, or 40 µm.

Suitable substrate materials include, but are not limited to transparent substrate such as polymers, plastics, glass, quartz, or other dielectric materials, nontransparent substrates including translucent or opaque plastics, silicon, metal, ceramic, and the like.

In various embodiments channel materials include, but are not limited to flexible polymers such as PDMS, plastics, and the like, and nonflexible materials such as stiff plastics, glass, silicon, quartz, metals, and the like.

In certain embodiments it is contemplated to use one or more of the switching devices described herein in a fluorescent activated cell sorter (FACS). It will, of course be recognized however, that the switch can be incorporated into numerous other microfluidic/microanalytical devices. The switch can be integrated with other microfluidic components such as PDMS channels, wells, valves for follow up analysis of sorted cells. The switch is well suited for use in lab-on-a-chip systems, cell sorters, and the like.

Microscale flow cytometers have been much sought after due to their abilities in handling small sample size and device miniaturization and integration. Our device can advance the speed of microscale flow cytometers and cell sorters by two orders of magnitude. This way the microscale flow cytometers can operate at a speed comparable to that of conventional flow cytometers while retaining its unique advantages, making them highly competitive to conventional flow cytometers currently on the market.

Figure 15A:
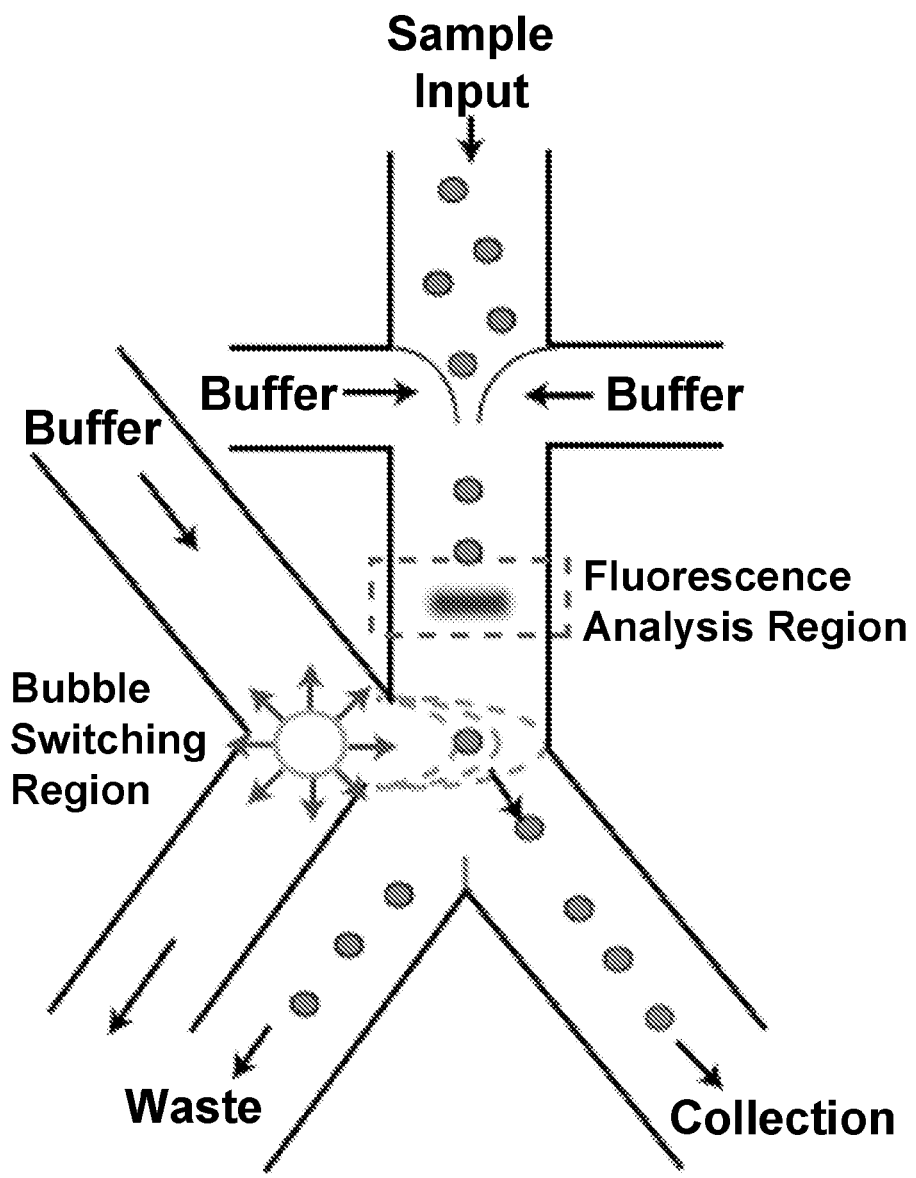
FIGS. 15A and 15B show schematic illustrations of a pulsed laser triggered fluorescence activated microfluidic sorter using sheath flow focusing.
Figure 15B:
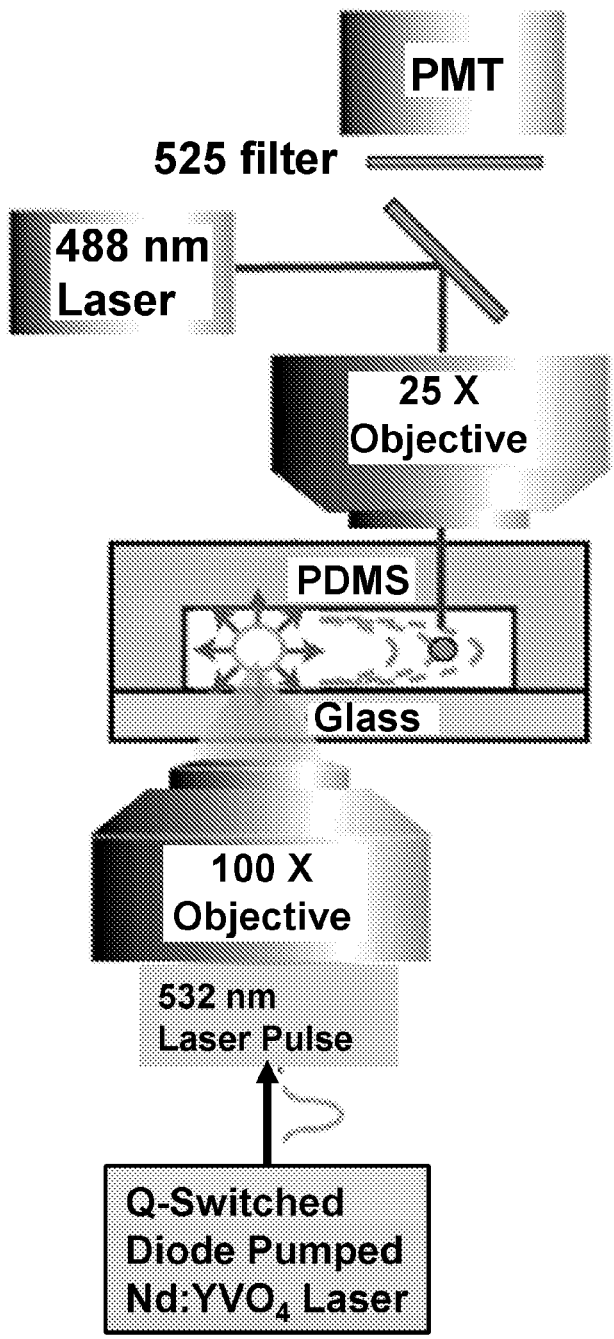

One illustrative microscale flow cytometer (FACs) system is schematically illustrated in FIGS. 15A and 15B which depict a pulsed laser triggered fluorescence activated microfluidic sorter using sheath flow focusing. The illustrated device consists of a main microchannel (or sample channel) with two outlets, collection and waste. Using sheath flow focusing, the input particles are focused slightly off the centerline of the main channel and go into the waste channel. Labeled particles (e.g., fluorescently tagged cells) are detected as they flow through the top of the Y junction. This triggers a laser pulse (e.g., a 488 nm Nd:YVO4 laser) focused through a high N.A. objective lens into the pulsed channel running in parallel with the main channel. The focused laser pulse induces optical breakdown of the liquid medium and the subsequent cavitation bubble. As the bubble expands, the surrounding liquid is pushed away and squeezed through the nozzle opening into the main channel. This liquid jet deflects the particle flow into the collection channel To induce cavitation bubbles, a pulsed laser (e.g., Q-switched Nd:YVO4 pulsed laser beam (EKSPLA, Jazz 20)) is focused through an objective lens (e.g., 100×, NA 0.9) into the pulsed channel. For sample fluorescence excitation, a second laser (e.g. a 10 mW, 488 nm solid state laser) is focused into the main channel through an objective lens on the other side of the microfluidic chip. The emitted sample fluorescence can be collected by the same objective lens and sent into a photomultiplier tube (PMT). Fluorescence intensity can be obtained by integrating PMT signal (e.g., every 10 µsec).

Figure 20:
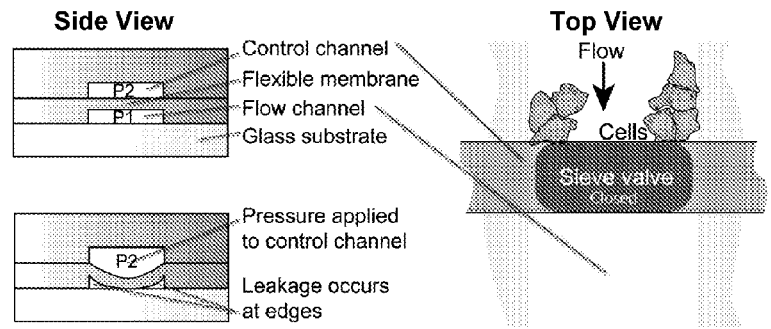
FIG. 20 illustrates one example of sieve valves that can be integrated for downstream cell trapping and release.

In certain embodiments, it is contemplated that sorting using the devices described herein can lead to cell/particle capture in "sieve" valves (i.e. filter) regions downstream on the same foundry chip. Sieve valves are standard foundry components that in essence are leaky valves that leave behind a narrow path for fluid flow that allows for continuous flow and trapping of cells. Cells are too large to squeeze through this gap as shown in FIG. 20. Types of sieve valves are versatile and many of them are compatible with standard foundry fabrication processes and can be selected to meet different downstream requirements (Zhong et al. (2008) *Lab on a Chip*, 8: 68-74; Zhong et al. (2008) *Curr. Med. Chem.*, 15: 2897-2900; Marcus et al. (2006) *Anal. Chem.*, 78: 3084-3089; Wang et al. (2007) *Lab on a Chip*, 7: 740-745; Melin and Quake et al. (2007) *Ann. Rev. Biophys. Biomolecular Struct.*, 36: 213-231; Panaro et al. (2005) *Biomolecular Engineering*, 21: 157-162; Irimia and Toner (2006) *Lab on a Chip*, 6: 345-352). Aggregates of trapped cells can be released after sorting is complete for downstream expression analysis of the collected population, or individual cells of interest can be transported by optical tweezers into neighboring chambers for downstream single-cell analysis. Optical trapping and transport of single cells in microfluidic channels is routinely performed. In certain embodiments the FACS sorting system, optical trapping system, and the microfluidics system are all constructed on the same optical table.

As indicate above, the high speed switch described herein can provide a µFACs system integrated with other processing modules on a microfluidic "chip". Of course, use of the switch need not be limited to particle/cell sorting. The switch can be exploited for use in any of a number of high-speed microfluidic switching applications.

Figure 21A:
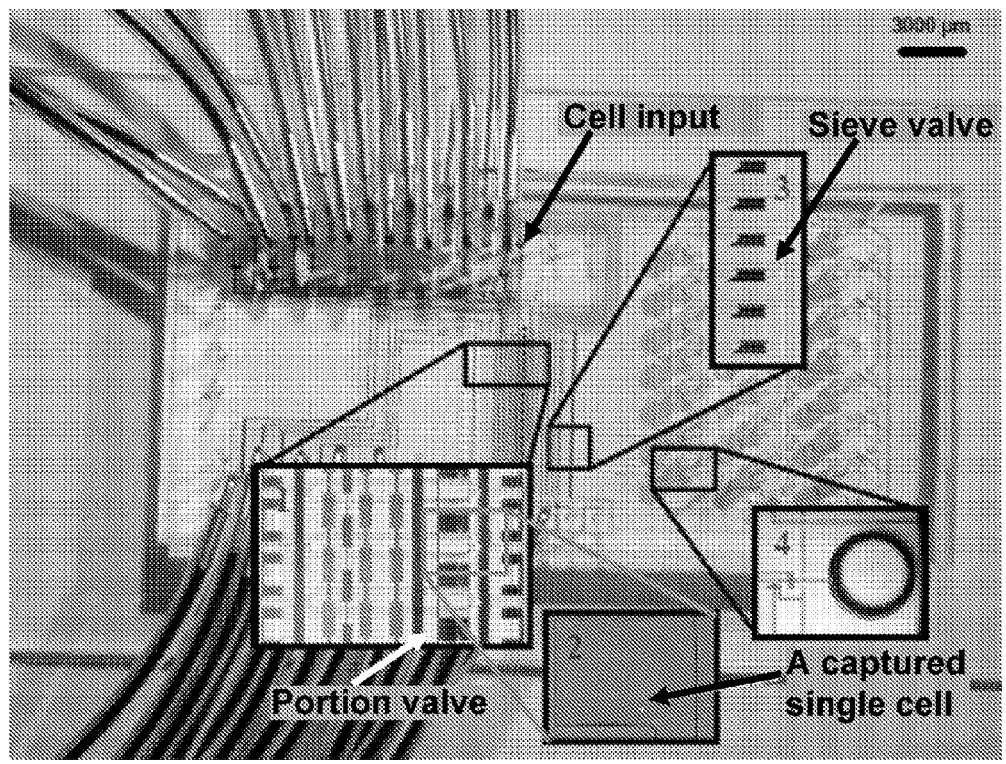
FIG. 21A illustrates a single-cell mRNA extraction microfluidic device filled with food dye for illustration.
Figure 21B:
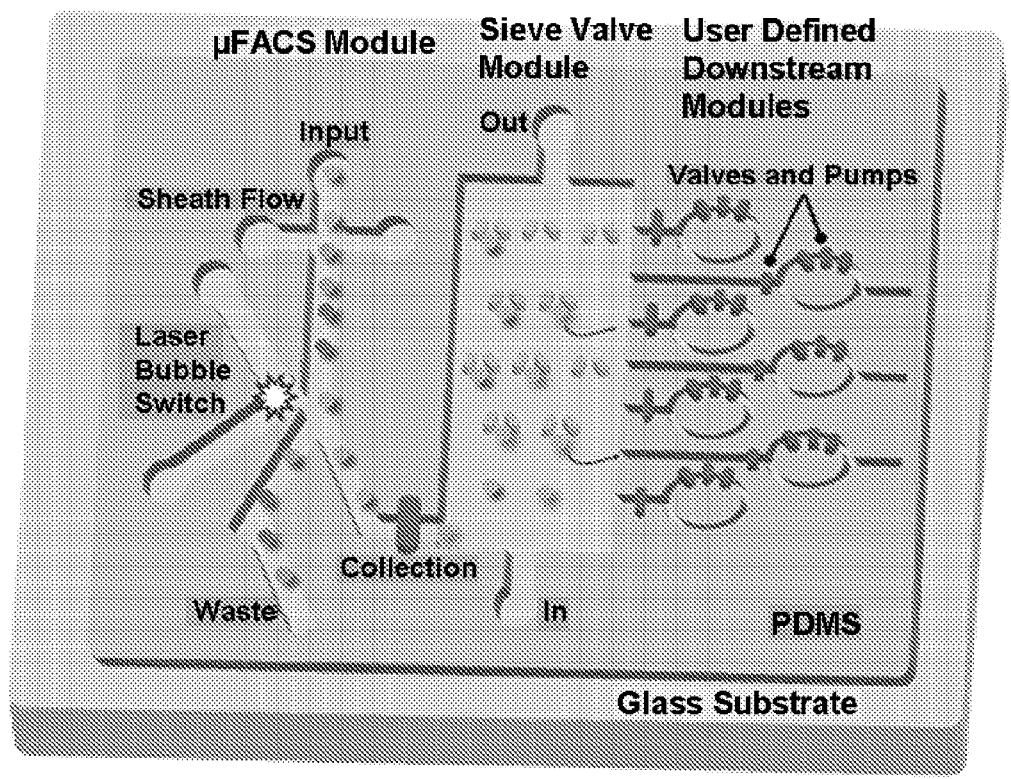
FIG. 21B illustrates a schematic of a high-speed microfluidic fluorescence activated cell sorter integrated on standard single-layer or multilayer PDMS based microfluidic chip. The illustrated chip includes three modules, a μFACS module, a cell capture module, and a user defined downstream module that allows performing multistep lab on a chip analysis of sorted cells in sterile environment.

For example, microfluidic devices can manipulate volumes as small as several nanoliters. Because the microfluidic reaction volume is close to the size of single mammalian cells, material loss is minimized in single-cell mRNA analysis with these devices. The ability to process live cells inside microfluidic devices provides a great advantage for the study of single-cell transcriptomes because mRNA is rapidly degraded with cell death. A highly integrated microfluidic device, having 26 parallel 10 nL reactors for the study of gene expression in single human embryonic stem cells (hESC) has been reported (Zhong et al. (2008) *Lab on a Chip*, 8: 68-74; Zhong et al. (2008) *Curr. Med. Chem.*, 15: 2897-2900). As shown in FIG. 21B, all stems for obtaining single-cell cDNA including cell capture, mRNA capture/purification, cDNA synthesis/purification, are performed inside the device. This microfluidic device currently consists of several modules including (1) multiplexed microfluidic control valves, (2) sieve valves for cell capture, and (3) chambers for cell lysis and mRNA extraction. In various embodiments the µFACS module can be added before the sieve valve module as the fourth module and optical tweezers can be used to deliver single cells trapped in the sieve valves into chambers, which greatly simplifies the microfluidic structure by completely removing the complex microfluidic circuits required for single cell transport. The schematic diagram of the high speed µFACS integrated single cell analysis platform is presented in FIG. 21A. The illustrated chip includes three modules, a µFACS module, a cell capture module, and a user defined downstream module that allows performing multistep lab on a chip analysis of sorted cells in sterile environment. This Figure is intended to be illustrative and not limiting. Using the teachings provided herein, numerous integrated lab-on-a-chip systems can be fabricated.

Any of a number of approaches can be used to convey the liquid mixture of particles or cells along the channels of the devices described herein. Such approaches include, but are not limited to syringe pumps, peristaltic pumps, electrokinetic pumps, bubble pumps, air pressure driven pumps, and gravity-driven pumps.

The parameters described above and in the Examples (e.g., flow rate, dye concentration, cell concentration, fluorescence detection time, delay time for triggering laser cavitation, etc.) can be varied to optimize high speed cell sorting on foundry fabricated PDMS microfluidic chips (or in other chips). In certain embodiments the flow speed of the main channel will be kept around 1 m/sec. With a standard 40 μm channel height provided by the design rules from the foundry, a 100 μm wide channel provides a flow rate of 0.24 mL/minute. If a standard cell concentration of $2.5 \times 10^6$ cells/mL is used, the corresponding sorting speed is 10,000 cells/sec. The average separation distance between cells is 100 μm, which is 5 times larger than the width of a liquid jet; and the average arrival time between two neighboring cells is 100 μsec, which is 10 times longer than the proposed 10 μsec perturbation time. The short perturbation time and small perturbation volume of our laser cavitation induced fluid jet provides sufficient design margin to achieve 10,000 cell/sec sorting throughput on foundry microfluidic chips. A higher speed can potentially be achieved with optimized operation parameters.

There are many formats, materials, and size scales for constructing the high-speed switches described herein, the FACs systems described herein and various integrated fluidic systems, In certain embodiments the devices described herein invention (including the microfluidic channels) are to be made of PDMS (or other polymers), fabricated using a technique called "soft lithography". P DMS is an attractive material for a variety of reasons including, but not limited to: (i) low cost; (ii) optical transparency; (iii) ease of molding; (iv) elastomeric character; (v) surface chemistry of oxidized PDMS can be controlled using conventional siloxane chemistry; (vi) compatible with cell culture (non-toxic, gas permeable). Soft lithographic rapid prototyping can be employed to fabricate the desired microfluidic channel systems.

Figure 14A:
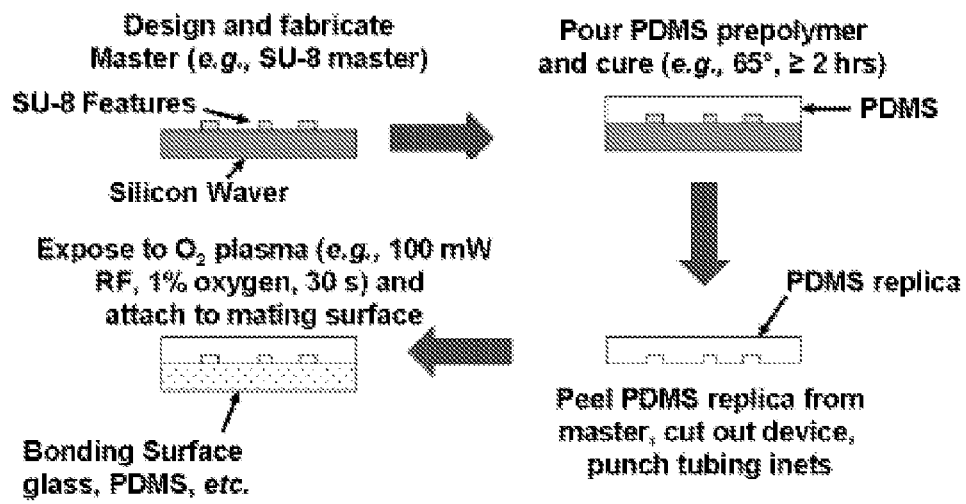
FIG. 14A shows a schematic overview of PDMS device fabrication.

One illustrative version of soft lithographic methods is illustrated in FIG. 14A. The key features of this method involve preparing a master (mold) (e.g., an SU-8 master) to form the microchannel system, pouring a pre-polymer onto the master and curing it to form a cured patterned replica (e.g., PDMS polymer replica), removing the replica from the master and trimming and punching tubing inlets as required, optionally exposing the polymer to a plasma (e.g., to an $O_2$ plasma) and optionally bonding the polymer to a substrate (e.g., a glass substrate).

Figure 14B:
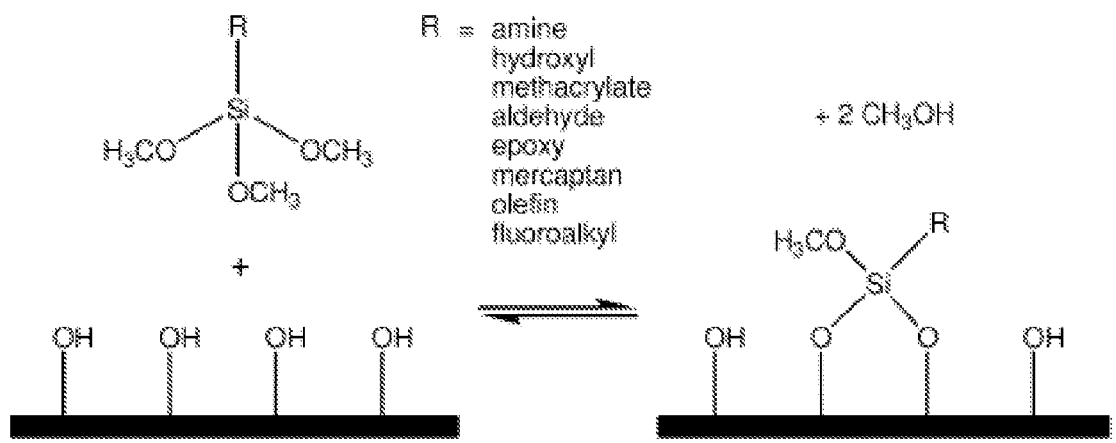
FIG. 14B illustrates the silanization of plasma-exposed PDMS.

Another useful property of PDMS and other polymers is that their surface can be chemically modified in order to obtain the interfacial properties of interest (see, e.g., Makamba et al. (2003) *Electrophoresis*, i24(21): 3607-3619). On illustrative method of covalently functionalizing PDMS is to expose it to an oxygen plasma, whereby surface Si—$CH_3$ groups along the PDMS backbone are transformed into Si—OH groups by the reactive oxygen species in the plasma. These silanol surfaces are easily transformed with alkoxysilanes to yawed many different chemistries as shown in FIG. 14B (see, e.g., *Silicon Compounds Silanes and Silicones*, Gelest, Inc.: Morrisville, Pa., 2004; p. 560; Hermanson et al. (1992) *Immobilized affinity ligand techniques*, Academic Press, San Diego, Calif. 1992).

The master mold is typically a micromachined mold. Molds can be patterned by any of a number of methods known to those of skill in the in the electronics and micromachining industry. Such methods include, but are not limited to wet etching, electron-beam vacuum deposition, photolithography, plasma enhanced chemical vapor deposition (PECVD), molecular beam epitaxy, reactive ion etching (RIE), and/or chemically assisted ion beam milling (CAIBM techniques), and the like (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*, and the like).

Another illustrative micromachining method uses a high-resolution transparency film as a contact mask for a thick photoresist layer. Multilayer soft lithography improves on this approach by combining soft lithography with the capability to bond multiple patterned layers of elastomer. Basically, after separate curing of the layers, an upper layer is removed from its mold and placed on top of the lower layer, where it forms a hermetic seal. Further curing causes the two layers to irreversibly bond. This process creates a monolithic three-dimensionally patterned structure composed entirely of elastomer. Additional layers are added by simply repeating the process. The ease of producing multilayers makes it possible to have multiple layers of fluidics, a difficult task with conventional micromachining.

In various embodiments, single-layer or multi-layer PDMS devices are contemplated. In illustrative approach, a network of microfluidic channels is designed in a CAD program. This design is converted into a transparency by a high-resolution printer; this transparency is used as a mask in photolithography to create a master in positive relief photoresist. PDMS cast against the master yields a polymeric replica containing a network of channels. The surface of this replica, and that of a flat slab of PDMS, can be oxidized in an oxygen plasma. These oxidized surfaces seal tightly and irreversibly when brought into conformal contact. Oxidized PDMS also seals irreversibly to other materials used in microfluidic systems, such as glass, silicon, silicon oxide, and oxidized polystyrene. Oxidation of the PDMS has the additional advantage that it yields channels whose walls are negatively charged when in contact with neutral and basic aqueous solutions; these channels support electroosmotic pumping and can be filled easily with liquids with high surface energies (especially water).

The fabrication methods described herein are illustrative and not limiting. Using the teachings provided herein, numerous other photolithographic and/or micromachining techniques can be used to fabricate the devices described herein. The micromachining and soft lithography methods described above, as well as many others, are well known to those of skill in the art (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*; McDonald et al. (2000) *Electrophoresis*, 21(1): 27-40).

EXAMPLES

The following examples are offered to illustrate, but not to limit the claimed invention.

Example 1

Performance of a μFACS Using a Pulsed Laser Switch

FIGS. 15A and 15B schematically illustrate a pulsed laser triggered fluorescence activated microfluidic cell sorter incorporating the switching device described herein. The device consists of a main microchannel (or sample channel) with two outlets, collection and waste. Using sheath flow focusing, the input particles are focused slightly off the centerline of the main channel and go into the waste channel. Fluorescent particles are detected as they flow through the top of the Y junction. This triggers a laser pulse focused through a high N.A. objective lens into the pulsed channel running in parallel with the main channel. The focused laser pulse induces optical breakdown of the liquid medium and the subsequent cavitation bubble. As the bubble expands, the surrounding liquid is pushed away and squeezed through the nozzle opening into the main channel. This liquid jet deflects the particle flow into the collection channel.

To induce cavitation bubbles, a Q-switched Nd:YVO$_4$ pulsed laser beam (EKSPLA, Jazz 20) was focused through an objective lens (100×, NA 0.9) into the pulsed channel. The pulse was 15 nsec in pulse width and 532 nm in wavelength with a pulse repetition rate up to 100 kHz. The pulse energy used was 88 µJ. For sample fluorescence excitation, a 10 mW, 488 nm solid state laser was focused into the main channel (spot size ~50 µm in diameter) through a 25×, NA 0.4 objective lens on the other side of the microfluidic chip. The emitted sample fluorescence was collected by the same objective lens and sent into a photomultiplier tube (PMT; Sens-Tech, P30CWAD5). Fluorescence intensity was obtained by integrating PMT signal every 10 µsec. Codes written in LabView 8.2 were programmed into FPGA logic to perform real-time detection, threshold comparison and timed triggering of the pulsed laser.

Figure 16:
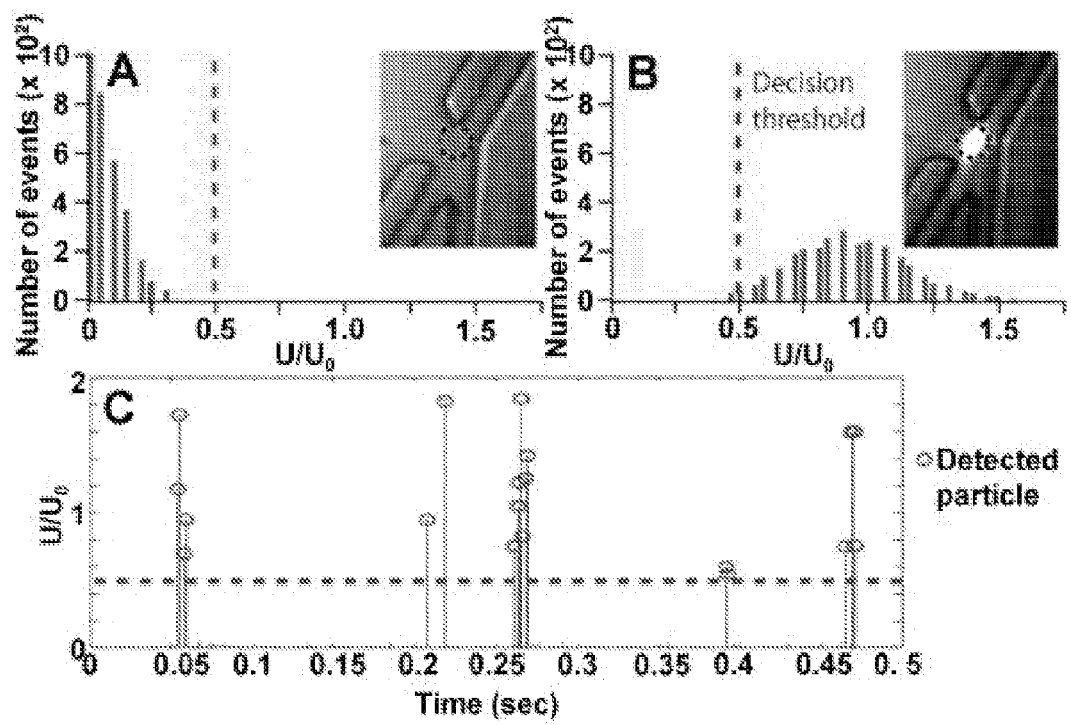
FIG. 16, panels A and B show histograms of fluorescent signals from the background (panel A), and 10 μm green fluorescent beads (panel B). Panel C: Time series of the fluorescent signals.

FIG. 16, panels A-C, show the fluorescent signal detection in the system. Panels A and B are the histograms of the background and the fluorescence intensity of 10 µm green microspheres respectively. In panel C fluorescence signal over a period of 0.5 sec was plotted. Particles flowing through the detection zone could be distinguished from the background noise based on the predetermined decision threshold.

Figure 17:
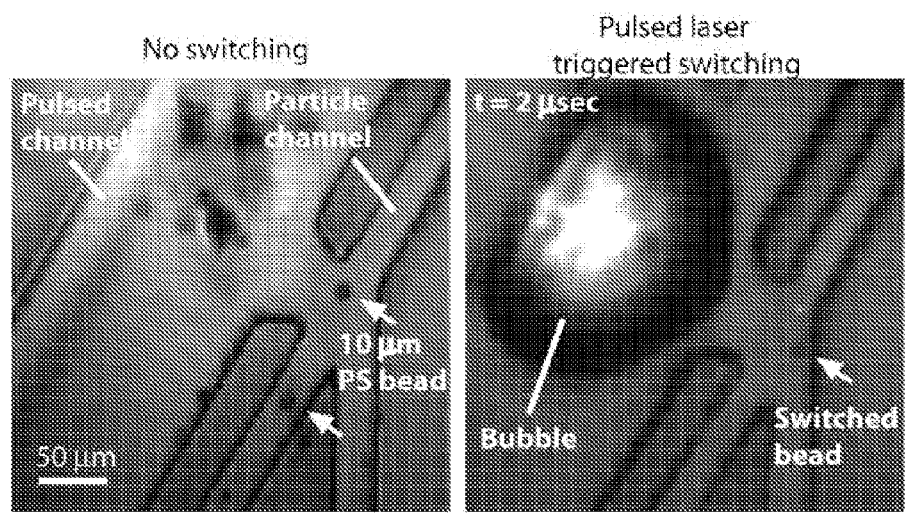
FIG. 17 show particle switching triggered by a focused pulsed laser beam. The bead is pushed to move for 30 μm in 2 μsec.

FIG. 17 demonstrates particle switching at the Y junction triggered by a single laser pulse. Without switching, the particles flow to the waste channel on the left as shown in a time-resolved image. A cavitation bubble induced by the focused laser pulse (taken 2 µsec after the laser pulse arrival) pushed the liquid flow into the main channel through a 50 µm wide nozzle to deflect the particle for 30 µm in 2 µsec towards the collection channel. The bubble lifetime characterized by the time-resolved images was 50 µsec and the perturbation volume is tens of nanoliters.

Cell Viability.

To test cell viability after sorting, HeLa cells were trypsinized and pumped into the sample channel. Switched cells from collection outlet were stained with propidium iodide and checked for fluorescence. An 88% cell viability of switched cells was obtained.

Device Reliability.

The current device has been tested for 100 million cycles at a pulsing rate of 10,000 bubbles/sec without showing any observable failure.

Inertial Focusing and Cell Viability

As discussed further below in certain embodiments, inertial focusing (Hur et al. (2010) *Lab on a Chip,* 10: 274-280; Di Carlo et al. (2007) *Proc. Natl. Acad. Sci., USA,* 104: 18892-18897) can be utilized as a cell positioning mechanism in the systems described herein. Importantly, in certain embodiments, sorted cells are available downstream and on-chip for biomolecular analysis including gene expression analysis. Therefore using microarrays we investigated gene expression changes elicited by the inertial focusing process.

The overall gene expression profile of MCF7 (breast cancer) cells before and after flow through the inertial focusing system showed only minor changes. Unsupervised clustering using the 284 most differentially expressed annotated genes (1734 probe sets) was performed to determine whether cells flowed through the device have globally distinct gene expression profiles. Hierarchical clustering showed that control and flow samples (C and F) and 24 hour samples were clustered together, indicating that the gene expression profiles for processed MCF7 cells were not globally distinct from the control samples. Also, the 24 hr C/24 hr F samples clustered closely together suggesting that there might be a long term incubation effect. Moreover, gene filtering between control and flow samples using a t-test ($p<0.05$) and the fold-change criterion (2 fold-change) showed that no single gene was differentially expressed between those samples. We conclude that there are no significant alterations caused by initially flowing cells through an inertial focusing device as evidenced by no differences in gene expression at 2-fold change.

Reduce Laser-Induced Bubble Size Resulting Fluid, Particle, and Cell Interactions The principle of high speed microfluidic actuation is based on the fast energy absorption and releasing processes of laser induced cavitation. The light induced water breakdown is a nonlinear optical process that needs strong instant light intensity to occur. The threshold pulse energy required to induce a cavitation bubble in pure water using a 6 nsec, 532 nm laser pulse focused to a submicron spot is around 1 µJ, resulting in an extremely high instantaneous power (>1000 W) flow into a 1 femtoliter volume at the focal point. Even when only ~1% optical energy is absorbed and converted into bubble expansion, the energy density is several orders of magnitude higher than any known physical mechanisms demonstrated in prior microfluidic actuations can possibly achieve.

However, the minimum threshold energy required for nonlinear optical absorption limits the minimum bubble size to a few hundreds of micrometers in our preliminary data, which gives our FACS a large perturbation volume and long perturbation time. Furthermore, the 2D sheath flow focusing in our current FACS also limits the fluorescence detection and the synchronization of laser bubble triggering. Cells focused in a plane intercept varying magnitude velocity streams and thus travel downstream at different velocities.

To reduce the threshold of pulse energy and the bubble size, light-absorbing dyes can be added in the bubble excitation channel. Table 1 presents the preliminary testing results which shows the bubble size can be successfully decreased to 66.7 µm, corresponding to less than 1 nanoliter perturbation volume, with a complete bubble cycle of 7 µsec. Smaller bubble size can be achieved simply by increasing dye concentration. For cells running in the main sorting channel at a speed of 1 m/sec, lateral cell displacement of 3.3 µm and 20 µm has been observed for the 66.7 µm and 111.7 µm bubbles, respectively, in the current device configuration.

TABLE 1

Small bubble generation in water with light-absorbing dyes and the corresponding lateral cell displacement.

| Pulse energy (µJ) | Cell Displacement (µm) | Max Bubble Diameter (µm) | Bubble Lifetime (µs) |
|---|---|---|---|
| 25 | 3.3 | 66.7 | 7 |
| 41 | 10 | 94.2 | 13 |
| 59 | 20 | 111.7 | 20 |

Theoretical fluidic dynamics predicts that a particle of 10 µm in diameter at rest takes ~5 µsec to reach the same flow speed as the fluid in a microfluidic channel. Prior literature has shown that a laser induced bubble can transport a 10 µm HeLa cell for a 25 μm distance within 200 nsec without severe damage such as cell lysis (however, transient cell permeability was observed in that experiment). This experiment shows that ultrafast cell steering is possible with laser induced bubble techniques. Such a fast movement shows that the dynamics of particles and cells is different from the flow dynamics.

Cell Viability.

The effects of strong shear stress on cells can be categorized in three different levels. For shear stress above 200 kPa, most mammalian cells are lysed instantly. It is been shown that when the tensile strain on a cell membrane is larger than 2~3%, the membrane is irreversibly ruptured. Reducing the shear stress to tens of kPa, the cell membrane become transiently permeable and small molecules or dyes can diffuse across the membrane through these tiny holes. Technologies such as optoporation and sonoportation have utilized this phenomenon for introducing extracellular contents such as DNA into cells (El-Sayed and El-Sayed (2006) *Cancer Letters,* 239: 129-135; Huang et al. (2006) *Abst. Papers of the Am. Chem. Soc.,* 231, March 2006; Pitsillides et al. (2003) Biophys. J., 84: 4023-4032; Yao et al. (2005) *J. Biomed. Opt.,* 10; 064012).

Figure 18:
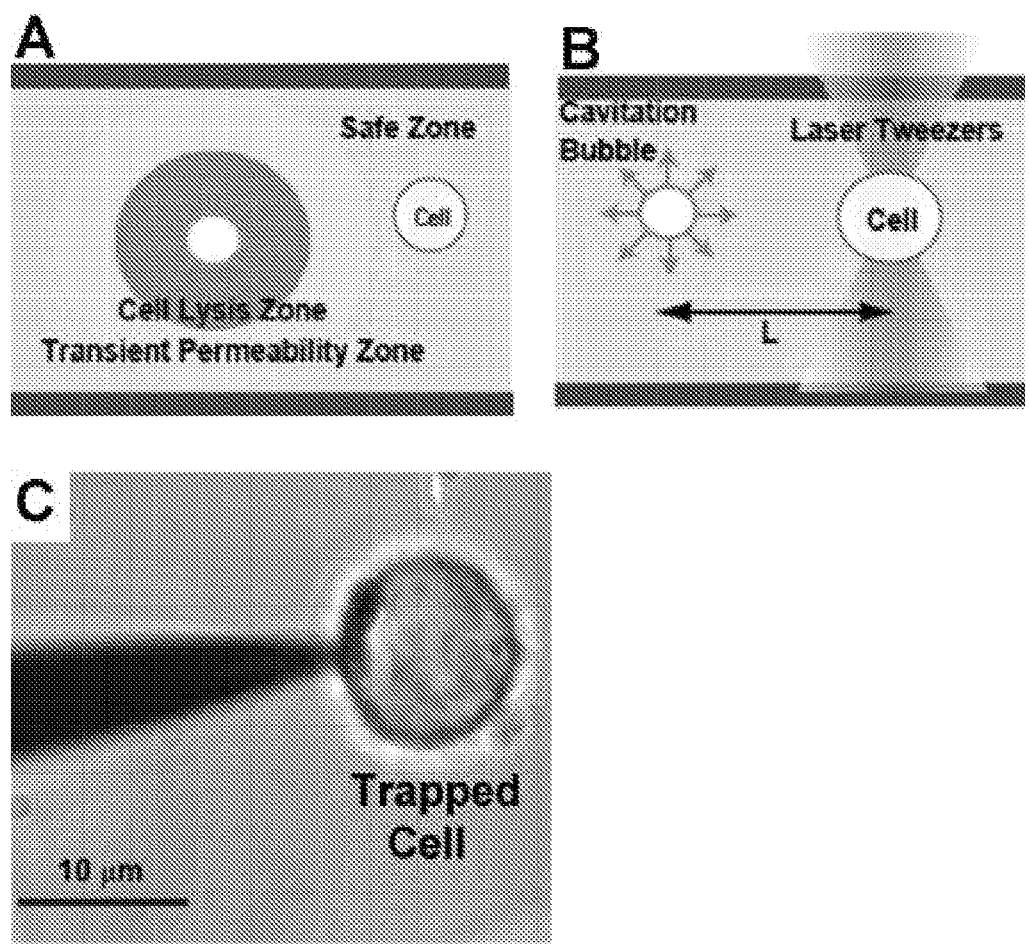
FIG. 18, panel A shows a schematic of the three zones (cell lysis, transient permeability, safe) for cells positioned near a rapidly expanding cavitation bubble. Panel B show that optical tweezers can be used to precisely position a cell in three-dimensional space to test the range of these three zones. Panel C demonstrates a non-adherent cell trapped and positioned by optical tweezers integrated on the same system illustrated in FIGS. 15A and 15B.

FIG. 18, panel A illustrates the three zones (cell lysis, transient membrane permeability, and safe zones) near a laser induced cavitation bubble. To precisely position a cell at desired locations near a bubble for cell viability analysis, an optical tweezers illustrated in FIG. 18, panel B, has been integrated with this laser pulsing and imaging system described herein. FIG. 18, panel C, demonstrates optical trapping of a Nalm-6 cell in this system and a capillary glass pipette is used to test the stiffness of the trap.

To study the cell membrane transient permeability during sorting processes, a membrane impermeant fluorescent Calcein dye can be loaded in the flow channel together with cells. Cells with transient membrane permeability due to strong shear stress can uptake these dyes and fluoresce green. To investigate the possibility of delayed cell death (apoptosis), annexin V/propidium iodide staining can be applied to monitor cell death up to 24 hours after pulsing.

μFACS Using 3D Inertial Focusing

Figure 19A:
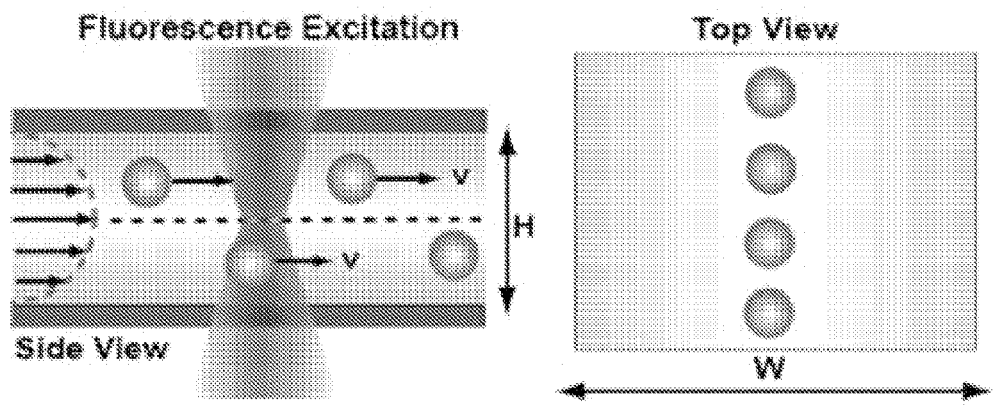
FIG. 19A, shows a schematic of inertial focusing of particles in a straight microfluidic channel with high aspect ratio (H:W=1:2) viewed from the side (left) and top (right).
Figure 19B:
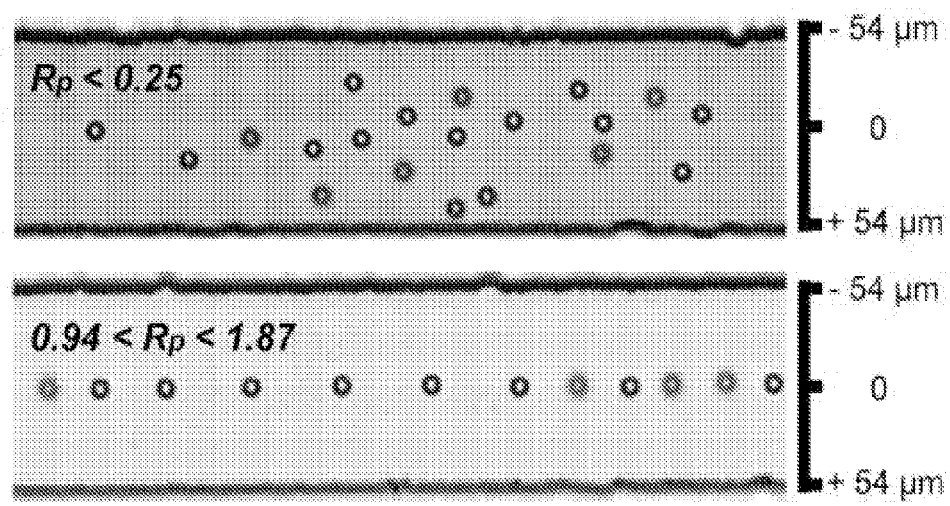
FIG. 19B shows high-speed microscopic images illustrating flow speed dependence of particle alignment in the z direction. At low flow rates, Rp<0.25, flowing particles are randomly distributed while at moderate flow rates, 0.94<Rp<1.87, particles aligned into a single train.

In order to provide uniform velocities for cells prior to sorting and assist with synchronization of laser pulsing, inertial focusing can be implemented in the microchannel system. Inertial focusing is a sheathless hydrodynamic method of focusing cells and particles to a limited number of streamlines that correspond with channel symmetry (Hur et al. (2010) *Lab on a Chip,* 10: 274-280; Di Carlo et al. (2007) *Proc. Natl. Acad. Sci., USA,* 104: 18892-18897). Inertial focusing to two cell streams can be easily achieved in high-aspect ratio channels. The challenge to implement this in foundry-fabricated chips is to achieve high-aspect ratio while observing the design rules of the foundry. For the Stanford foundry, design rules include: (i) a largest aspect ratio of 1:1, (ii) lowest aspect ratio of 1:10 (H:W), (iii) maximum channel height of 45 μm. The optimal design therefore that also satisfies inertial focusing criteria will likely consist of a low ~1:2 aspect ratio (which alone yields two focusing positions at the top and bottom of the channel as shown in FIG. 19). Cells focused in these two streams flow at the same speed due to the symmetric channel configuration and velocity profile. For optical excitation, fluorescence detection, bubble perturbation, cells in these two streams will see no difference by focusing the excitation and imaging plane in the middle height of the channel. Sheath flows can also be introduced in the upper stream to focus cells in the lateral direction and rely on inertial focusing for z direction positioning. This hybrid method can reduce the channel length for inertial focusing and shorten the traveling distance of cells in the lateral direction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A high-speed microfluidic switch, said switch comprising:
    a first microfluidic channel comprising a bifurcation into a first path and a second path;
    a liquid or gel filled second microfluidic channel adjacent to said first microfluidic channel where said liquid or gel flows through said second microfluidic channel and said second microfluidic channel is disposed such that formation of a gas or plasma cavitation bubble in the liquid or gel in said second microfluidic channel redirects particles flowing into said first path so they flow into said second path;
    a pulse laser focused on said second microfluidic channel and configured to provide sufficient energy to form said cavitation bubble;
    wherein said switch comprises a wall between said second channel and said first channel where said second microfluidic channel and said wall are disposed such that formation of a gas or plasma bubble in said second channel deforms said wall to redirect particles flowing into said first path so they flow into said second path.

2. A high-speed microfluidic switch, said switch comprising:
    a first microfluidic channel comprising a bifurcation into a first path and a second path;
    a liquid or gel filled second microfluidic channel adjacent to said first microfluidic channel and disposed such that formation of a gas or plasma cavitation bubble in the liquid or gel in said second microfluidic channel redirects particles flowing into said first path so they flow into said second path, wherein said liquid or gel comprises light-absorbing dye molecules or nanoparticles;
    a wall or a port, or a channel between said second channel and said first channel; and
    a pulse laser focused on said second microfluidic channel and configured to provide sufficient energy to form said cavitation bubble.

3. A method for detecting or sorting particles or cells, said method comprising:
    flowing said particles or cells through a switch according to claim 2; and
    activating said pulse laser to form a cavitation bubble that channels desired particles into a desired flow path.

4. A high-speed microfluidic switch, said switch comprising:
    a first microfluidic channel comprising a bifurcation into a first path and a second path;
    a second microfluidic channel adjacent to said first microfluidic channel;
    a connecting port or channel connecting said second microfluidic channel to said first microfluidic channel;
    a liquid or gel-filled third microfluidic channel adjacent to said second microfluidic channel disposed such that the formation of a cavitation bubble in the liquid or gel in said third channel induces a fluid flow or pressure through said connecting port or channel that redirects particles flowing into said first path so they flow into said second path, wherein said liquid or gel comprises light-absorbing dye molecules or nanoparticles; and a pulse laser focused on said third microfluidic channel and configured to provide sufficient energy to form said cavitation bubble.

5. A method for detecting or sorting particles or cells, said method comprising:

flowing said particles or cells through a switch according to claim 4; and activating said pulse laser to form a cavitation bubble that channels desired particles into a desired flow path.

6. The switch according to any one of claims 1, 2, or 4, wherein said first microfluidic channel is a Y-shaped microchannel.

7. The switch according to any one of claims 1, 2, or 4, wherein said first microfluidic channel is formed from an elastomeric material.

8. The switch of claim 7, wherein said elastomeric material is PDMS.

9. The switch according to any one of claims 1, 2, or 4, wherein said laser provides a pulse energy and frequency to permit switching of particles from said first path to said second path in a time of less than 100 μ sec.

10. The switch of claim 9, wherein said laser provides a pulse energy and frequency to permit switching of particles from said first path to said second path in a time of less than 70 μ sec or less.

11. The switch according to any one of claims 1, 2, or 4, wherein said liquid or gel is a liquid.

12. The switch according to any of claims 1, 2, or 4, wherein said switch is disposed on a substrate comprising a material selected from the group consisting of a polymer, a plastic, a glass, quartz, a dielectric material, a semiconductor, silicon, germanium, ceramic, and a metal or metal alloy.

13. The switch according to any of claims 1, 2, or 4, wherein said switch is integrated with other microfluidic components selected from the group consisting of PDMS channels, wells, and/or valves.

14. The switch according to any of claims 1, 2, or 4, wherein said switch is a component of a lab-on-a-chip.

15. The switch according to any of claims 1, 2, or 4, wherein said switch is a component of a cell sorter.

16. A system for controlling microfluidic flow, said system comprising a switch according to any of claims 1, 2, or 4, and components for detecting particles or cells in said system.

17. A method for detecting or sorting particles or cells, said method comprising:

flowing said particles or cells through a switch according to any of claim 1, 2, or 4; and activating said pulse laser to form a cavitation bubble that channels desired particles into a desired flow path.

* * * * *